US008611983B2

(12) United States Patent
Glossop

(10) Patent No.: US 8,611,983 B2
(45) Date of Patent: Dec. 17, 2013

(54) METHOD AND APPARATUS FOR GUIDING AN INSTRUMENT TO A TARGET IN THE LUNG

(75) Inventor: Neil David Glossop, Toronto (CA)

(73) Assignee: Philips Electronics Ltd, Vancouver, British Columbia (CA)

( * ) Notice: Subject to any disclaimer, the term of this patent is extended or adjusted under 35 U.S.C. 154(b) by 1520 days.

(21) Appl. No.: 11/333,363

(22) Filed: Jan. 18, 2006

(65) Prior Publication Data

US 2006/0184016 A1   Aug. 17, 2006

Related U.S. Application Data

(60) Provisional application No. 60/644,018, filed on Jan. 18, 2005, provisional application No. 60/676,310, filed on May 2, 2005.

(51) Int. Cl.
*A61B 5/05* (2006.01)

(52) U.S. Cl.
USPC ............................ 600/424; 600/414; 600/426

(58) Field of Classification Search
USPC .......................... 600/424, 426, 427, 428, 414
See application file for complete search history.

(56) References Cited

U.S. PATENT DOCUMENTS

| | | | |
|---|---|---|---|
| 3,021,842 A | 2/1962 | Flood | |
| 4,080,706 A | 3/1978 | Heilman et al. | 29/173 |
| 4,279,252 A | 7/1981 | Martin | 128/349 R |
| 4,697,595 A | 10/1987 | Breyer et al. | 128/660 |
| 4,722,056 A | 1/1988 | Roberts et al. | 364/413 |
| 4,777,951 A | 10/1988 | Cribier et al. | 128/344 |
| 4,887,606 A | 12/1989 | Yock et al. | 128/662.05 |
| 4,895,168 A | 1/1990 | Machek | 128/772 |
| 4,935,019 A | 6/1990 | Papp, Jr. | 604/362 |
| 4,961,433 A | 10/1990 | Christian | 128/772 |
| 5,014,708 A | 5/1991 | Hayashi et al. | 128/653 R |
| 5,042,486 A | 8/1991 | Pfeiler et al. | 128/653 R |
| 5,045,080 A | 9/1991 | Dyer et al. | 604/362 |
| 5,085,659 A | 2/1992 | Rydell | 606/47 |
| 5,116,345 A | 5/1992 | Jewell et al. | 606/130 |

(Continued)

FOREIGN PATENT DOCUMENTS

| | | |
|---|---|---|
| AU | 6367896 | 2/1997 |
| AU | 722539 | 8/2000 |

(Continued)

OTHER PUBLICATIONS

TRA029—RITA StarBurst Soft Tissue Access System and RITA StarBurst Hard Tissue Access System, http://www.ritamedical.com, Rita Medical Systems, Inc., copyright 2002, , 8 pages.

(Continued)

*Primary Examiner* — Unsu Jung
*Assistant Examiner* — Christopher Cook

(57) ABSTRACT

The invention provides methods and apparatus for navigating a medical instrument to a target in the lung. In one embodiment, the invention includes inserting a bronchoscope into the lung, inserting a catheter into the lung through the working channel of the bronchoscope, inserting a tracked navigation instrument wire into the lung through the catheter, navigating the tracked navigation instrument through the lung to the target, advancing the catheter over the tracked navigation instrument to the target, removing the tracked navigation instrument from the catheter, and inserting a medical instrument into the catheter, thus bringing the medical instrument in proximity to the target.

21 Claims, 10 Drawing Sheets

(56) References Cited

U.S. PATENT DOCUMENTS

| | | | |
|---|---|---|---|
| 5,187,658 A | 2/1993 | Cline et al. | 364/413.13 |
| 5,204,625 A | 4/1993 | Cline et al. | 324/306 |
| 5,207,675 A | 5/1993 | Canady | 606/40 |
| 5,211,165 A | 5/1993 | Dumoulin et al. | 128/653.1 |
| 5,221,283 A | 6/1993 | Chang | 606/130 |
| 5,247,935 A | 9/1993 | Cline et al. | 128/653.2 |
| 5,251,127 A | 10/1993 | Raab | 364/413.13 |
| 5,251,635 A | 10/1993 | Dumoulin et al. | 128/653.2 |
| 5,255,680 A | 10/1993 | Darrow et al. | 128/653.1 |
| 5,265,610 A | 11/1993 | Darrow et al. | 128/653.1 |
| 5,271,400 A | 12/1993 | Dumoulin et al. | 128/653.2 |
| 5,275,165 A | 1/1994 | Ettinger et al. | 128/653.2 |
| 5,290,266 A | 3/1994 | Rohling et al. | 604/272 |
| 5,291,010 A | 3/1994 | Tsuji | 250/208.1 |
| 5,291,890 A | 3/1994 | Cline et al. | 128/653.2 |
| 5,304,933 A | 4/1994 | Vavrek et al. | 324/318 |
| 5,305,203 A | 4/1994 | Raab | 364/413.13 |
| 5,307,812 A | 5/1994 | Hardy et al. | 128/653.1 |
| 5,318,025 A | 6/1994 | Dumoulin et al. | 128/653.2 |
| 5,323,779 A | 6/1994 | Hardy et al. | 128/653.2 |
| 5,327,884 A | 7/1994 | Hardy et al. | 128/653.2 |
| 5,353,808 A | 10/1994 | Viera | 128/772 |
| 5,365,927 A | 11/1994 | Roemer et al. | 128/653.2 |
| 5,368,031 A | 11/1994 | Cline et al. | 128/653.2 |
| 5,368,032 A | 11/1994 | Cline et al. | 128/653.2 |
| 5,377,678 A | 1/1995 | Dumoulin et al. | 128/653.1 |
| 5,383,454 A | 1/1995 | Bucholz | 128/653.1 |
| 5,383,465 A | 1/1995 | Lesny et al. | 128/662.05 |
| 5,386,828 A | 2/1995 | Owens et al. | 128/653.1 |
| 5,389,101 A | 2/1995 | Heilbrun et al. | 606/130 |
| 5,391,199 A | 2/1995 | Ben-Haim | 607/122 |
| 5,396,905 A | 3/1995 | Newman et al. | 128/849 |
| 5,400,383 A | 3/1995 | Yassa et al. | 378/98.2 |
| 5,437,277 A | 8/1995 | Dumoulin et al. | 128/653.1 |
| 5,443,066 A | 8/1995 | Dumoulin et al. | 128/653.1 |
| 5,443,068 A | 8/1995 | Cline et al. | 128/653.5 |
| 5,445,150 A | 8/1995 | Dumoulin et al. | 128/653.1 |
| 5,465,732 A | 11/1995 | Abele | 128/772 |
| 5,480,382 A | 1/1996 | Hammerslag et al. | 604/95 |
| 5,490,840 A | 2/1996 | Uzgiris et al. | 604/22 |
| 5,493,598 A | 2/1996 | Yassa et al. | 378/98.2 |
| 5,526,812 A | 6/1996 | Dumoulin et al. | 128/653.1 |
| 5,526,814 A | 6/1996 | Cline et al. | 128/653.2 |
| 5,558,091 A | 9/1996 | Acker et al. | 128/653.1 |
| 5,603,318 A | 2/1997 | Heilbrun et al. | 128/630 |
| 5,645,065 A | 7/1997 | Shapiro et al. | 128/653.1 |
| 5,646,524 A | 7/1997 | Gilboa | 324/207.17 |
| 5,646,525 A | 7/1997 | Gilboa | 324/207.17 |
| 5,647,373 A | 7/1997 | Paltieli | 128/749 |
| 5,705,014 A | 1/1998 | Schenck et al. | 156/272.4 |
| 5,713,858 A | 2/1998 | Heruth et al. | 604/93 |
| 5,715,166 A | 2/1998 | Besl et al. | 364/474.24 |
| 5,715,822 A | 2/1998 | Watkins et al. | 128/653.5 |
| 5,740,802 A | 4/1998 | Nafis et al. | 128/653.1 |
| 5,749,835 A | 5/1998 | Glantz | 600/424 |
| 5,769,790 A | 6/1998 | Watkins et al. | 600/439 |
| 5,769,861 A | 6/1998 | Vilsmeier | 606/130 |
| 5,848,969 A | 12/1998 | Panescu et al. | 600/462 |
| 5,857,032 A | 1/1999 | Wang et al. | 382/154 |
| 5,868,673 A | 2/1999 | Vesely | 600/407 |
| 5,873,845 A | 2/1999 | Cline et al. | 601/3 |
| 5,880,976 A | 3/1999 | DiGioia, III et al. | 364/578 |
| 5,931,786 A | 8/1999 | Whitmore, III et al. | 600/459 |
| 5,944,023 A | 8/1999 | Johnson et al. | 128/899 |
| 5,978,696 A | 11/1999 | VomLehn et al. | 600/411 |
| 6,016,439 A | 1/2000 | Acker | 600/411 |
| 6,036,682 A | 3/2000 | Lange et al. | 604/529 |
| 6,073,043 A | 6/2000 | Schneider | 600/424 |
| 6,097,978 A | 8/2000 | Demarais et al. | 600/429 |
| 6,106,476 A | 8/2000 | Corl et al. | 600/486 |
| 6,141,576 A | 10/2000 | Littmann et al. | 600/381 |
| 6,147,480 A | 11/2000 | Osadchy et al. | 324/67 |
| 6,165,184 A | 12/2000 | Verdura et al. | 606/148 |
| 6,188,355 B1 | 2/2001 | Gilboa | 342/448 |
| 6,196,980 B1 | 3/2001 | Akerfeldt et al. | 600/585 |
| 6,203,493 B1 | 3/2001 | Ben-Haim | 600/117 |
| 6,203,543 B1 | 3/2001 | Glossop | 606/60 |
| 6,205,411 B1 | 3/2001 | DiGioia, III et al. | 703/11 |
| 6,210,339 B1 | 4/2001 | Kiepen et al. | 600/486 |
| 6,216,029 B1 | 4/2001 | Paltieli | 600/427 |
| 6,226,543 B1 | 5/2001 | Gilboa et al. | 600/407 |
| 6,233,476 B1 | 5/2001 | Strommer et al. | 600/424 |
| 6,235,038 B1 | 5/2001 | Hunter et al. | 606/130 |
| 6,241,690 B1 | 6/2001 | Burkett et al. | 600/585 |
| 6,266,551 B1 | 7/2001 | Osadchy et al. | 600/424 |
| 6,266,552 B1 | 7/2001 | Slettenmark | 600/424 |
| 6,272,370 B1 | 8/2001 | Gillies et al. | 600/411 |
| 6,272,371 B1 | 8/2001 | Shlomo | 600/424 |
| 6,285,898 B1 | 9/2001 | Ben-Haim | 600/374 |
| 6,285,903 B1 | 9/2001 | Rosenthal et al. | 600/433 |
| 6,288,785 B1 | 9/2001 | Frantz et al. | 356/614 |
| 6,308,089 B1 | 10/2001 | von der Ruhr et al. | 600/338 |
| 6,314,310 B1 | 11/2001 | Ben-Haim et al. | 600/424 |
| 6,317,621 B1 | 11/2001 | Graumann et al. | 600/424 |
| 6,332,089 B1 | 12/2001 | Acker et al. | 600/424 |
| 6,336,906 B1 | 1/2002 | Hammarstrom et al. | 600/585 |
| 6,338,716 B1 | 1/2002 | Hossack et al. | 600/459 |
| 6,356,783 B1 | 3/2002 | Hubbard, Jr. | 600/546 |
| 6,380,732 B1 | 4/2002 | Gilboa | 324/207.17 |
| 6,381,485 B1 * | 4/2002 | Hunter et al. | 600/407 |
| 6,383,174 B1 | 5/2002 | Eder | 606/1 |
| 6,385,482 B1 | 5/2002 | Boksberger et al. | 600/424 |
| 6,427,079 B1 | 7/2002 | Schneider et al. | 600/424 |
| 6,442,417 B1 | 8/2002 | Shahidi et al. | 600/429 |
| 6,468,265 B1 | 10/2002 | Evans et al. | 606/1 |
| 6,473,635 B1 | 10/2002 | Rasche | 600/428 |
| 6,484,118 B1 | 11/2002 | Govari | 702/150 |
| 6,493,589 B1 | 12/2002 | Medhkour et al. | 607/99 |
| 6,498,944 B1 | 12/2002 | Ben-Haim et al. | 600/407 |
| 6,499,488 B1 | 12/2002 | Hunter et al. | 128/899 |
| 6,500,114 B1 | 12/2002 | Petitto et al. | 600/156 |
| 6,512,958 B1 | 1/2003 | Swoyer et al. | 607/117 |
| 6,529,758 B2 | 3/2003 | Shahidi | 600/407 |
| 6,547,782 B1 | 4/2003 | Taylor | 606/14 |
| 6,558,333 B2 | 5/2003 | Gilboa et al. | 600/466 |
| 6,574,492 B1 | 6/2003 | Ben-Haim et al. | 600/374 |
| 6,574,498 B1 | 6/2003 | Gilboa | 600/424 |
| 6,580,938 B1 | 6/2003 | Acker | 600/424 |
| 6,585,654 B2 | 7/2003 | White et al. | 600/463 |
| 6,588,333 B1 | 7/2003 | Homer et al. | 101/32 |
| 6,591,127 B1 | 7/2003 | McKinnon | 600/411 |
| 6,591,129 B1 | 7/2003 | Ben-Haim et al. | 600/424 |
| 6,593,884 B1 | 7/2003 | Gilboa et al. | 342/448 |
| 6,615,155 B2 | 9/2003 | Gilboa | 702/150 |
| 6,619,838 B2 | 9/2003 | Bencini et al. | 378/190 |
| 6,628,987 B1 | 9/2003 | Hill et al. | 607/9 |
| 6,690,963 B2 | 2/2004 | Ben-Haim et al. | 600/424 |
| 6,702,780 B1 | 3/2004 | Gilboa et al. | 604/95.04 |
| 6,711,429 B1 | 3/2004 | Gilboa et al. | 600/407 |
| 6,719,700 B1 | 4/2004 | Willis | 600/462 |
| 6,735,471 B2 | 5/2004 | Hill et al. | 607/2 |
| 6,748,112 B1 | 6/2004 | Nguyen et al. | 382/203 |
| 6,753,873 B2 | 6/2004 | Dixon et al. | 345/542 |
| 6,782,287 B2 | 8/2004 | Grzeszczuk et al. | 600/424 |
| 6,783,536 B2 | 8/2004 | Vilsmeier et al. | 606/130 |
| 6,785,571 B2 | 8/2004 | Glossop | 600/424 |
| 6,788,967 B2 | 9/2004 | Ben-Haim et al. | 600/424 |
| 6,792,303 B2 | 9/2004 | Taimisto | 600/424 |
| 6,893,429 B2 | 5/2005 | Petersen | 604/537 |
| 6,895,268 B1 | 5/2005 | Rahn et al. | 600/429 |
| 6,916,290 B2 | 7/2005 | Hedengren et al. | 600/549 |
| 7,085,400 B1 | 8/2006 | Holsing et al. | 382/103 |
| 7,386,339 B2 | 6/2008 | Strommer et al. | 600/424 |
| 7,570,791 B2 | 8/2009 | Frank et al. | 382/132 |
| 2001/0008972 A1 | 7/2001 | Gielen | 607/45 |
| 2001/0011175 A1 | 8/2001 | Hunter et al. | 606/130 |
| 2001/0031919 A1 | 10/2001 | Strommer et al. | 600/424 |
| 2001/0031985 A1 | 10/2001 | Gilboa et al. | 607/1 |
| 2001/0036245 A1 | 11/2001 | Kienzle, III et al. | 378/4 |
| 2001/0038354 A1 | 11/2001 | Gilboa | 342/450 |
| 2001/0039419 A1 | 11/2001 | Francischelli et al. | 606/42 |
| 2001/0047133 A1 | 11/2001 | Gilboa et al. | 600/429 |
| 2002/0005719 A1 | 1/2002 | Gilboa et al. | 324/309 |
| 2002/0038102 A1 | 3/2002 | McFarlin et al. | 604/30 |

(56) References Cited

U.S. PATENT DOCUMENTS

| | | | |
|---|---|---|---|
| 2002/0042571 A1 | 4/2002 | Gilboa et al. | 600/429 |
| 2002/0049375 A1 | 4/2002 | Strommer et al. | 600/407 |
| 2002/0049451 A1 | 4/2002 | Parmer et al. | 606/108 |
| 2002/0062203 A1 | 5/2002 | Gilboa | 702/150 |
| 2002/0074005 A1 | 6/2002 | Hogg et al. | 128/899 |
| 2002/0087101 A1 | 7/2002 | Barrick et al. | 600/587 |
| 2002/0143317 A1 | 10/2002 | Glossop | 604/529 |
| 2002/0156363 A1 | 10/2002 | Hunter et al. | 600/410 |
| 2002/0156417 A1 | 10/2002 | Rich et al. | 604/65 |
| 2002/0165448 A1 | 11/2002 | Ben-Haim et al. | 600/424 |
| 2002/0165468 A1 | 11/2002 | Tolkowsky et al. | 600/587 |
| 2003/0018251 A1 | 1/2003 | Solomon | 600/427 |
| 2003/0021455 A1 | 1/2003 | Dixon et al. | 382/132 |
| 2003/0028233 A1 | 2/2003 | Vardi et al. | 623/1.11 |
| 2003/0030004 A1 | 2/2003 | Dixon et al. | 250/370.09 |
| 2003/0051733 A1* | 3/2003 | Kotmel et al. | 128/207.14 |
| 2003/0074011 A1 | 4/2003 | Gilboa et al. | 606/130 |
| 2003/0092988 A1 | 5/2003 | Makin | 600/439 |
| 2003/0114778 A1 | 6/2003 | Vilsmeier et al. | 600/585 |
| 2003/0114846 A1 | 6/2003 | Fuimaono et al. | 606/41 |
| 2003/0130576 A1 | 7/2003 | Seeley et al. | 600/426 |
| 2003/0171680 A1 | 9/2003 | Paltieli | 600/459 |
| 2003/0171739 A1 | 9/2003 | Murphy et al. | 606/1 |
| 2003/0208102 A1 | 11/2003 | Gilboa | 600/41 |
| 2003/0208296 A1 | 11/2003 | Brisson et al. | 700/117 |
| 2003/0216639 A1 | 11/2003 | Gilboa et al. | 600/424 |
| 2003/0220557 A1 | 11/2003 | Cleary et al. | 600/409 |
| 2004/0019274 A1 | 1/2004 | Galloway, Jr. et al. | 600/425 |
| 2004/0024309 A1 | 2/2004 | Ferre et al. | 600/424 |
| 2004/0034297 A1 | 2/2004 | Darrow et al. | 600/407 |
| 2004/0034500 A1 | 2/2004 | Verard et al. | 600/424 |
| 2004/0036867 A1 | 2/2004 | Jedamzik et al. | 356/243.1 |
| 2004/0077942 A1 | 4/2004 | Hall et al. | 600/428 |
| 2004/0078036 A1 | 4/2004 | Keidar | 606/41 |
| 2004/0097804 A1 | 5/2004 | Sobe | 600/424 |
| 2004/0097805 A1 | 5/2004 | Verard et al. | 600/428 |
| 2004/0097806 A1 | 5/2004 | Hunter et al. | 600/434 |
| 2004/0138548 A1 | 7/2004 | Strommer et al. | 600/407 |
| 2004/0143188 A1 | 7/2004 | Barzell et al. | 600/439 |
| 2004/0147837 A1 | 7/2004 | Macaulay et al. | 600/424 |
| 2004/0147939 A1 | 7/2004 | Rabkin et al. | 606/108 |
| 2004/0158146 A1 | 8/2004 | Mate et al. | 600/427 |
| 2004/0199072 A1* | 10/2004 | Sprouse et al. | 600/424 |
| 2004/0221853 A1 | 11/2004 | Miller | 128/207.14 |
| 2004/0234953 A1 | 11/2004 | Dawson et al. | 434/262 |
| 2004/0249267 A1 | 12/2004 | Gilboa | 600/424 |
| 2004/0254458 A1 | 12/2004 | Govari | 600/437 |
| 2005/0033149 A1 | 2/2005 | Strommer et al. | 600/407 |
| 2005/0038337 A1 | 2/2005 | Edwards | 600/424 |
| 2005/0049520 A1 | 3/2005 | Nakao | 600/562 |
| 2005/0054900 A1 | 3/2005 | Mawn et al. | 600/156 |
| 2005/0059886 A1 | 3/2005 | Webber | 600/426 |
| 2005/0085715 A1 | 4/2005 | Dukesherer et al. | 600/424 |
| 2005/0085720 A1 | 4/2005 | Jascob et al. | 600/424 |
| 2005/0085793 A1 | 4/2005 | Glossop | 604/529 |
| 2005/0107688 A1 | 5/2005 | Strommer | 600/424 |
| 2005/0137661 A1* | 6/2005 | Sra | 607/96 |
| 2005/0182295 A1* | 8/2005 | Soper et al. | 600/117 |
| 2005/0182319 A1 | 8/2005 | Glossop | 600/424 |
| 2005/0228270 A1 | 10/2005 | Lloyd et al. | 600/424 |
| 2005/0239685 A1* | 10/2005 | Ingenito | 514/2 |
| 2006/0147100 A1 | 7/2006 | Fitzpatrick | 382/131 |
| 2007/0032862 A1 | 2/2007 | Weber et al. | 623/1.34 |

FOREIGN PATENT DOCUMENTS

| | | |
|---|---|---|
| BR | 9609484 | 12/1999 |
| CA | 2226938 | 2/1997 |
| DE | 69420228 | 9/1999 |
| DE | 69420228 T | 4/2000 |
| DE | 19845267 C1 | 5/2000 |
| EP | 0 845 959 | 6/1998 |
| EP | 0 654 244 | 8/1999 |
| EP | 1 466 552 | 10/2004 |
| IL | 0107523 | 1/2000 |
| IL | 0114610 | 7/2000 |
| JP | 10-277047 | 10/1998 |
| JP | 2000500031 T | 1/2000 |
| JP | 2005152463 | 6/2005 |
| WO | WO 97/03609 | 2/1997 |
| WO | WO 98/56295 | 12/1998 |
| WO | WO 00/22904 | 4/2000 |

OTHER PUBLICATIONS

TRA030—Cool-tip RF Tissue Ablation System, Cool-tip RF System, and Cool-tip Electrodes, http://www.valleylab.com/static/cooltip/products.html, Valleylab, copyright 2004, 4 pages.

TRA031—LeVeen Needle Electrode, Boston Scientific, printed from http://www.bostonscientific.com/med_specialty/deviceDetail.jhtml?task=_tskBasicDevice . . . , printed on Sep. 13, 2004, 1 page.

TRA032—Bradford J. Wood et al., "Navigation with Electromagnetic Tracking for Interventional Radiology Procedures: A Feasibility Study", Laboratory Investigations, *Journal of Vasc. Interv. Radiol.*, vol. 16, 2005, pp. 493-505.

TRA001—Tanase, Define, et al., "Magnetic Sensors for Use on Guide Wires or Catheters", in *SeSens* 2001, in press 2002, pp. 868-872.

TRA002—Solomon, Stephen B., et al., "Three-Dimensional CT-Guided Bronchoscopy with a Real-Time Electromagnetic Position Sensor: A Comparison of Two Image Registration Methods", *Chest*, vol. 118, No. 6, Dec. 2000, pp. 1783-1787.

TRA003—Solomon, Stephen B., et al., "Real-Time Cardiac Catheter Navigation on Three-Dimensional CT Images", *Journal of Interventional Cardiac Electrophysiology*, vol. 8, 2003, pp. 27-36.

TRA004—Palti-Wasserman, Daphna, et al., "Identifying and Tracking a Guide Wire in the Coronary Arteries During Angioplasty from X-Ray Images", *IEEE Transactions on Biomedical Engineering*, vol. 44, No. 2, Feb. 1997, pp. 152-164.

TRA005—Baert, Shirley A. M., et al., "Endpoint Localization in Guide Wire Tracking During Endovascular Interventions", *Academic Radiology*, vol. 10, No. 12, Dec. 2003, pp. 1424-1432.

TRA006—Baert, Shirley A. M., et al., "Three-Dimensional Guide-Wire Reconstruction from Biplane Image Sequences for Integrated Display in 3-D Vasculature", *IEEE Transactions on Medical Imaging*, vol. 22, No. 10, Oct. 2003, pp. 1252-1258.

TRA007—Baert, Shirley A. M., et al., "Guide-Wire Tracking During Endovascular Interventions", *IEEE Transactions on Medical Imaging*, vol. 22, No. 8, Aug. 2003, pp. 965-972.

TRA008—Kobashi, Keiji, et al., "A New Biomechanical Model Based Approach on Brain Shift Compensation", *MICCAI 2003*, LNCS 2878, 2003, pp. 59-66.

TRA009—Timinger, Holger, et al., "Motion Compensation for Interventional Navigation on 3D Static Roadmaps Based on an Affine Model and Gating", *Physics in Medicine and Biology*, vol. 49, 2004, pp. 719-732.

TRA010—Lorigo, Liana M., et al., "Curves: Curve Evolution for Vessel Segmentation", *Medical Image Analysis*, vol. 5, 2001, pp. 195-206 (pp. 1-14).

TRA011—Chassat, Fabrice, et al., "Experimental Protocol of Accuracy Evaluation of 6-D Localizers for Computer-Integrated Surgery: Application to Four Optical Localizers", *MICCAI 98*, vol. 1496, Oct. 1998, Cambridge, Massachusetts U.S.A., pp. 277-284.

TRA012—Tsai, Roger Y., "A Versatile Camera Calibration Technique for High-Accuracy 3D Machine Vision Metrology Using Off-the-Shelf TV Cameras and Lenses", *IEEE Journal of Robotics and Automation*, vol. RA-3, No. 4, Aug. 1987, pp. 323-344.

TRA013—"Semi-Automatic Registration for Image Guided Surgery", Traxtal poster presented at CAOS '99 (Computer Assisted Orthopaedic Surgery, 4th International Symposium), MICCAI, Mar. 17-19, 1999, Davos, Switzerland, 1 page.

TRA014—Wu, Xiaohui, et al., "A Direction Space Interpolation Technique for Calibration of Electromagnetic Surgical Navigation Systems", Lecture Notes in Computer Science Medical Image Computing and Computer-Assisted Intervention, *MICCAI 2003*, LNCS 2879, Publisher: Springer-Verlag Heidelberg, 2003, pp. 215-222.

(56) References Cited

OTHER PUBLICATIONS

TRA015—Livyatan, Harel, "Calibration and Gradient-Based Rigid Registration of Fluoroscopic X-raysto CT, for Intra Operative Navigation", Master of Science Thesis, supervised by Prof. Leo Joskowicz, School of Computer Science and Engineering, The Hebrew University of Jerusalem, Israel, Jul. 27, 2003, 92 pages.

TRA016—SuperDimension, Ltd, web page, updated in Sep. 2005, 1 page.

TRA017—Schweikard, Achim, et al., "Robotic Motion Compensation for Respiratory Movement During Radiosurgery", *Computer Aided Surgery*, vol. 5, 2000, pp. 263-277.

TRA018—Solomon, Stephen B., et al., "Real-Time Bronchoscope Tip Localization Enables Three-Dimensional CT Image Guidance for Transbronchial Needle Aspiration in Swine", *Chest*, vol. 114, No. 5, Nov. 1998, pp. 1405-1410.

TRA020—Hofstetter, R., et al., "Fluoroscopy Based Surgical Navigation—Concept and Clinical Applications", Maurice E. Muller Institute for Biomechanics, University of Bern, Switzerland, 1997, 3 pages.

TRA021—Tapper, Michael, et al., "Problems Encountered in the Implementation of Tsai's Algorithm for Camera Calibration", *Proc. 2002 Australasian Conference on Robotics and Automation*, Auckland, Nov. 27-29, 2002, pp. 66-70.

TRA022—Summers, Ronald M., et al., "Colonic Polyps: Complementary Role of Computer-Aided Detection in CT Colonography", *Radiology*, vol. 225, No. 2, Nov. 2002, pp. 391-399.

TRA023—Hara, A. K., et al., "Reducing Data Size and Radiation Dose for CT Colonography", *AJR*, vol. 168, May 1997, pp. 1181-1184.

TRA024—Knaan, Dotan, et al., Effective Intensity-Based 2D/3D Rigid Registration Between Fluoroscopic X-Ray and CT, *MICCAI*, vol. 1, 2003, pp. 351-358.

TRA025—Gee, A. H., et al., "3D Ultrasound Probe Calibration Without a Position Sensor", CUED/F-INFENG/TR 488, University of Cambridge, Department of Engineering, Sep. 2004, 21 pages.

TRA026—Lindseth, Frank, et al., "Probe Calibration for Freehand 3D Ultrasound Reconstruction and Surgical Navigation", Dec. 2002, 27 pages.

TRA027—Fuchs, Henry, et al., "Towards Performing Ultrasound-Guided Needle Biopsies from Within a Head-Mounted Display", University of North Carolina, Department of Computer Science, 1996, 10 pages; [Lecture Notes in Computer Science; vol. 1131 archive Proceedings of the 4th International Conference on Visualization in Biomedical Computing table of contents, pp. 591-600 Year of Publication: 1996, ISBN:3-540-61649-7; Hamburg, Germany, Sep. 22-25, 1996).].

TRA028—Henry Fuchs, Andrei State, Mark A. Livingston, William F. Garrett, Gentaro Hirota, Mary Whitton and Etta D. Pisano (MD). "Virtual Environments Technology to Aid Needle Biopsies of the Breast: An Example of Real-Time Data Fusion." Proceedings of Medicine Meets Virtual Reality:4 (Jan. 17-20, 1996, San Diego, California), IOS Press, Amsterdam, Jan. 1996.

\* cited by examiner

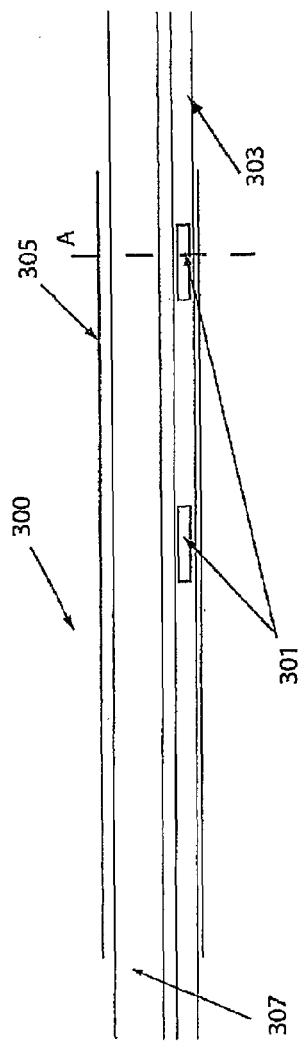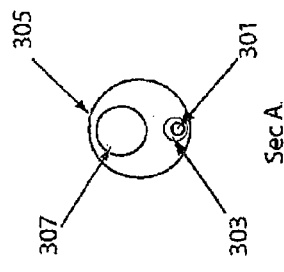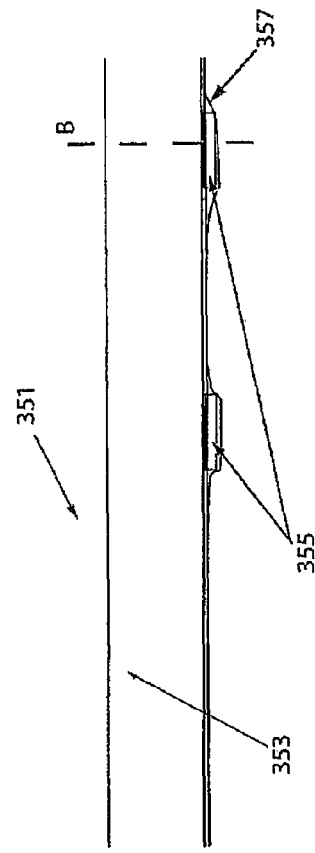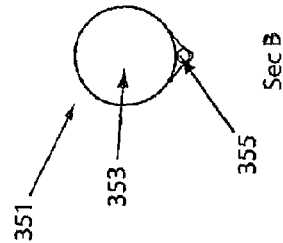
FIG. 3A
FIG. 3B
FIG. 3C
FIG. 3D

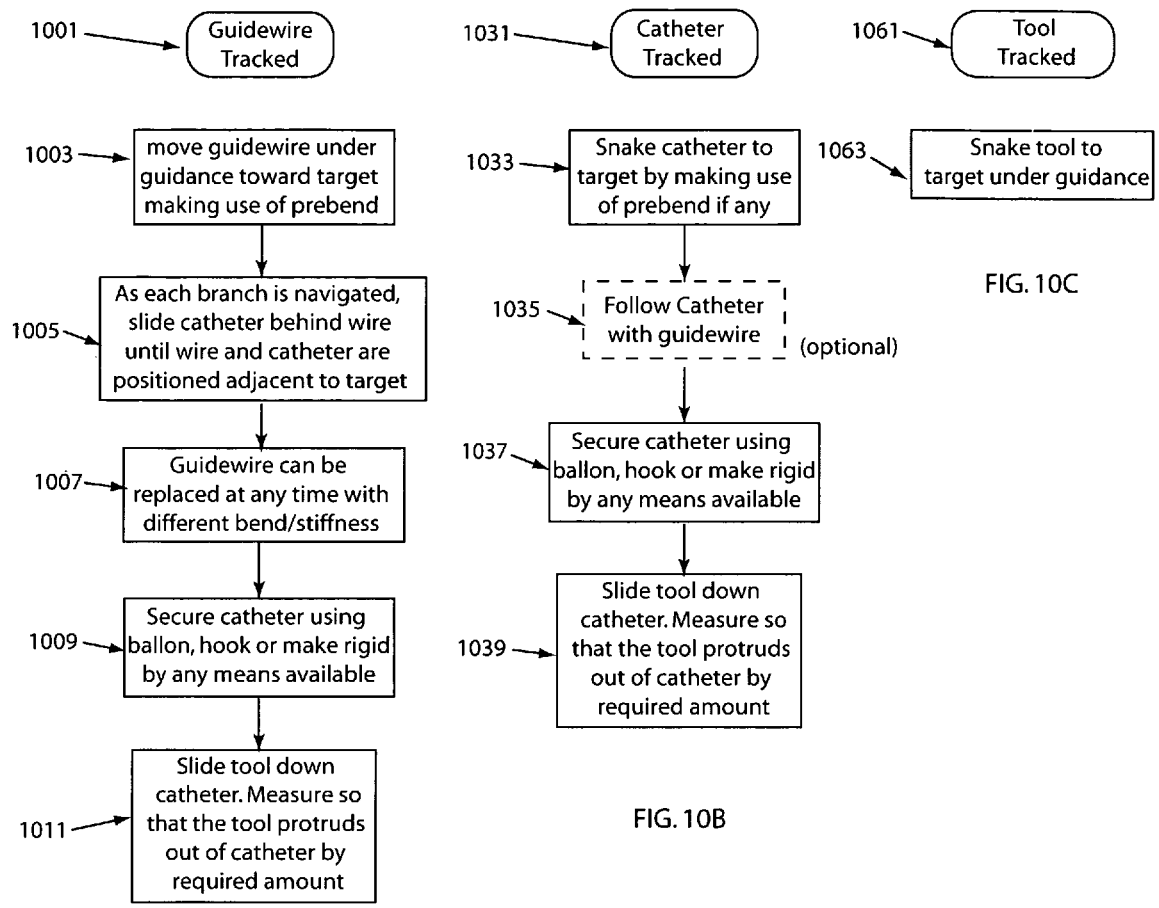

METHOD AND APPARATUS FOR GUIDING AN INSTRUMENT TO A TARGET IN THE LUNG

RELATED APPLICATIONS

This application claims priority to U.S. Provisional Patent Application Ser. No. 60/644,018, filed Jan. 18, 2005 and U.S. Provisional Patent Application Ser. No. 60/676,310, filed May 2, 2005, both of which are hereby incorporated by reference herein in their entirety.

FIELD OF THE INVENTION

This invention relates to a method and apparatus for guiding an instrument to a target in the lung.

BACKGROUND OF THE INVENTION

Navigation and access to areas of the lung typically involve the use of a Bronchoscope. FIG. 1 illustrates a typical bronchoscope 103 that can be used to navigate the lung 113 of a patient 112. Bronchoscopes typically contain an eye piece, such as, eyepiece 104. Alternatively, bronchoscopes may include a camera system in place of eyepiece 104, attached to eyepiece 104, or located distally near the tip of Bronchoscope 103. Bronchoscope 103 may also include a working channel 106 which may combine with bronchoscope 103 at a point 107. Working channel 106 may be a hollow channel into which instruments, fluids, samples, or other items or material can be inserted or withdrawn. Some bronchoscopes, especially fiber optic bronchoscopes or "fiberscopes" do not possess a working channel.

When using bronchoscope 103, patient 112 (in particular, lung 113) may first be scanned with an imaging modality such as, for example, a computerized tomography (CT) scan, a magnetic resonance (MR) scan, rotational fluoroscopy, or other imaging modality. This scan serves to identify a target 101, which may be a lesion, mass, tumor, or other item of interest. Once target 101 is identified on the scan, a possible access route 102 is selected for accessing target 101. Bronchoscope 103 is then advanced under visual guidance (and possibly fluoroscopic X-ray assistance) through the trachea 111 into different branches of the bronchial tree to a branch 108 that is near to target 101. Navigation into branch 108 brings tip 114 of bronchoscope 103 proximal to target 101. Tip 114 can then be secured in branch 108 by lodging tip 114 into branch 108 or by inflating a balloon or a cuff or by deploying hooks 109 or other restraints.

When bronchoscope 103 has arrived at target 101 or can no longer be advanced, an instrument for performing one or more procedures is then deployed through working channel 106 and advanced to branch 108 to perform the one or more procedures such as, lavage, biopsy, or other procedure on target 101. This is often very difficult because the tip of the instrument is outside of the visual range of bronchoscope 103. Positioning of the tip of the instrument is often augmented by fluoroscopy, but this may be of limited use because target 101 may be difficult to visualize by fluoroscopy. Additionally, it may be extremely difficult to localize target in three dimensions due to the planar nature of the fluoroscopic images. Ribs and the spine may obscure target 101 from view in the fluoroscopic images. Fluoroscopic images also do not depict the passageways in lung 113, and constant reference must be made to the scans (e.g., CT, MR, rotational fluoroscopy, or other scan) in an attempt to correlate the two image sets (e.g., the scans and the planar fluoroscopic images).

The invention addresses these and other problems by providing a computer assisted image-guided method and apparatus for targeted navigation to be used in conjunction with or as a replacement for bronchoscopy.

Image-guided surgery or computer assisted surgery uses pre-operative or inter-operative images of the patient to position a device or tool during surgery. First, a diagnostic image of the patient (or part thereof is obtained using an imaging modality such as, for example, CT, MR, ultrasound, X-ray, positron emission tomography (PET), or other imaging modality. The image is then transferred and stored on a computer.

The next step may be termed a "planning" step, which is often performed in some capacity. During planning, the image of the patient is examined and analyzed. The image of the patient may be processed to construct an enhanced image, such as a 3-D image, fused images, tri-planar views, or other enhanced images. Additionally, calculation or examination of the patient image may be performed to choose the best treatment option for an impending surgery, identify salient features of the anatomy, perform measurements, determine the geometry of implants, the extent of lesions, or to discern other information.

The patient may then be moved to an operating room equipped with a position sensor/tracking device such as a camera, magnetic field generator, or other tracking system. The tracking system may be connected to the computer with the patient image loaded on to it. The tracking system then tracks the position and/or orientation of position indicating elements attached to or within the patient's anatomy to determine the location and/or orientation of the anatomy. Additionally, any tools equipped with position indicating elements can also be tracked and their location and/or orientation can be displayed superimposed on the patient image that is displayed on a computer screen.

To perform these tasks, the processes of registration, motion compensation, and verification are undertaken. Registration refers to the process of matching the coordinate system in the operating room as defined by the position sensor/tracking device (e.g., the patient space) with the coordinate system in which the images were acquired (e.g., the image space). Registration is normally performed through a mathematical calculation of a "registration matrix" that can transform coordinates measured in the patient space into the image space or vice versa.

Motion compensation may be accomplished through dynamic referencing, which may be used to maintain registration even though the patient is moving in the operating room. Movement may occur, for example, from normal respiration, cardiac induced motion, bulk patient movement, or for other reasons. Dynamic referencing involves tracking the patient's motion throughout the surgical procedure using a dedicated position indicating element applied to the patient to monitor the motion of anatomy of the patient. Physiological state indicators may also be used either alone or in conjunction with dynamic referencing to monitor the physiologically induced motion such as may result from respiratory and/or cardiac motion. Physiological state indicators may themselves consist of dynamic referencing devices or a variety of other devices dedicated to measuring or reporting the state of a physiological parameter.

Verification is the process of ensuring that registration has been performed accurately and that dynamic referencing is adequately cancelling out the patient motion. This must be done prior to proceeding with the surgical procedure.

Additional detail regarding registration, motion compensation, dynamic referencing, verification, and image guided surgery techniques can be found in U.S. application Ser. No. 11/059,336 (published as U.S. Patent Publication No. 20050182319) by Glossop, which is incorporated by reference herein in its entirety.

SUMMARY OF THE INVENTION

The invention solves problems in the art by providing methods and apparatus for guiding a medical instrument to a target in the lung. The invention utilizes tracked elements along with navigation techniques to safely and accurately position an instrument in close proximity to a target or item of interest within the lung.

In one embodiment, an apparatus for guiding a medical instrument to a target in lung may include a bronchoscope with a working channel, a catheter or other hollow lumen serving as an extension of the bronchoscope's working channel, one or more dynamic referencing devices, a tracked "navigation instrument" such as, for example, a guidewire, a brush, or other instrument equipped with at least one trackable position indicating element, a "medical instrument" for performing a procedure, and/or other devices or elements. The apparatus may utilize a combination of some or all of the above devices to guide an instrument to a target in the lung and perform image-guided pulmonary treatment, investigation, or examination.

The bronchoscope (if used) in the apparatus of the invention may be the same as or similar to bronchoscopes known in the art such as, for example, bronchoscope 103 described in FIG. 1. The medical instrument for performing a procedure may include a biopsy device, a brush, a laser, an irrigation device, a radio frequency (RF) ablation device, an ultrasound probe, a bronchoscope, or other devices compatible with bronchoscope based examination, investigation or therapy. Typically, these devices are placed into the working channel or lumen of the bronchoscope or a lumen independently placed in the lung. They may optionally contain position indicating elements.

As used herein, position indicating elements refers to an element or sensor whose location, position, orientation, and/or coordinates relative to a tracking device/tracking system may be determined and recorded. A position indicating element may include, for example, a coil that may produce a magnetic field that is detectable by an electromagnetic tracking device. Other types of position indicating elements and/or tracking devices may be used. One of ordinary skill in the art will realize that any process, method, apparatus, system, or feature described herein that utilizes one or more position indicating elements may be assumed to also utilize a corresponding tracking system and any associated computer equipment necessary to facilitate the use thereof within the invention.

A tracked navigation instrument may include a guidewire having at least one position indicating element at or near its tip. In some embodiments, the tracked navigation instrument may include a bend near its tip. The tip may be also be tapered or of reduced diameter so as not to be as stiff as the shaft of the wire and/or may have a rounded end so as not to cause excessive trauma to the bronchial path though which it is navigated. In another embodiment, the tracked navigation instrument may also be the same medical instrument as used to perform the procedure.

In one embodiment, the apparatus for guiding an instrument to a target in the lung may include a catheter or other hollow lumen (herein referred to as the "catheter") that may serve as an extension of the working channel of the bronchoscope (or which may be the working channel of the bronchoscope). The catheter is constructed such that it can contain the tracked navigation instrument. The outer diameter of the catheter may be small enough to fit inside the working channel of the bronchoscope. The catheter's mechanical properties may enable it to follow the tracked navigation instrument as the tracked navigation instrument is advanced inside a patient's anatomy (e.g., inside the lung).

In one embodiment, the apparatus for guiding an instrument to a target in the lung may include one or more dynamic referencing devices. In some embodiments, some or all of the one or more dynamic referencing devices may each comprise a separate lumen that is inserted into a location in the patient's anatomy that will provide adequate sampling of patient motion so as to preserve a registration of the desired parts of the patient's anatomy. In one embodiment, the one or more dynamic referencing devices may each be equipped with one or more position indicating elements. Other devices may be used for dynamic referencing.

In some embodiments, physiological state indicators may be used as an alternative to or in addition to dynamic referencing. Physiological state indicators may include gating devices that provide a signal that enables synchronizing the acquisition of position/orientation information to the regular motion (e.g., heartbeat, respiration, or other repeated or cyclical motion) of the patient's anatomy. For example, when a signal indicating a particular part of the respiratory cycle is received, the image-guided system is instructed to begin acquiring valid position/orientation data regarding the position indicating elements included in the instruments being employed for the procedure. Once the respiratory cycle moves outside of that phase, a "stop" signal is issued to halt the data collection. In this way, it is not necessary to track the motion of the patient's anatomy if the respiratory motion is the only motion occurring. As mentioned above, physiological state indicators may be used in place of or in conjunction with dynamic referencing and may increase the accuracy of the system.

In one embodiment, the invention provides a method for guiding an instrument to a target in the lung of a patient. In one embodiment, registration of the patient may be first be performed. This registration of the patient's anatomy may utilize catheter "dragback" techniques, scope-dragback techniques, fiducial registration techniques, internal bronchial registration techniques, surface matching techniques, and/or other registration techniques.

In one embodiment, preparations may then be made for the mitigation of patient movement during subsequent navigation or procedures (e.g., dynamic referencing and/or physiological state indicators may be applied to the patient). In dynamic referencing, a dynamic referencing device is applied to the patient and used to compensate for chest and heart motion and/or various other patient motions in the region of interest. In some embodiments, the dynamic referencing device takes the form of a "dynamic referencing insert", such as a sleeve containing one or more position indicating elements that is placed into the working channel of a bronchoscope or endoscope. A dynamic referencing device can also be incorporated into a bronchoscope directly. Furthermore, a dynamic referencing device may also comprise or be placed inside a separate device such as a cannula, a catheter, a lumen, or other device that is introduced into a portion of the lung or blood vessel near the intervention site.

After preparation for mitigation of patient movement, the fidelity of the registration may be verified. There are several ways to verify registration, including, for example, touching a known location (e.g., a feature on the patient or a fiducial applied to the patient) with a tracked probe. The previously performed registration is then used to produce a reconstructed graphical icon representing the tip of the probe. This icon is examined see if it is indicated to touch the proper location (e.g., the known location that was touched). This may be repeated for several locations to determine if the system appears to be accurate. If the icon shows the probe tip touching the known location, the registration may be deemed accurate for that point. The process may be repeated for other points in the patient's anatomy. Other verification methods may be used.

After the registration has been verified, navigation of an instrument may be performed within the anatomy of the patient for the purposes of conducting a diagnostic, interventional, or other medical procedure. First, a bronchoscope may be inserted into the lung as close as possible to a target. In some embodiments, the target may comprise a lesion, a mass, a tumor, or other item of interest. In some embodiments, the bronchoscope may be so inserted prior to preparation for dynamic referencing and verification if registration In one embodiment, a catheter may then be inserted into the working channel of the bronchoscope and navigated past the end of bronchoscope further in the lung towards the target. Then a tracked navigation instrument (e.g., a guidewire equipped with one or more position indicating elements, at least one being located at or near the tip of the guidewire) is inserted into the catheter and advanced toward the target. This may involve navigating the tracked navigation instrument past the end of the catheter in the lung further towards the target. In one embodiment, the catheter may be inserted independently, without the use of the bronchoscope The tracked navigation instrument is then precisely navigated towards the target with navigational assistance from an image guided workstation (computer) that tracks and displays the position and/or orientation of the one or more position indicating elements of the tracked navigation instrument. The tracked navigation instrument may have a small bend (e.g., 20-45 degrees or other geometry) near the tip to facilitate this navigation. The technique of advancing the tracked navigation instrument may involve identifying the intended path of the navigation instrument and navigating the intended path by carefully rotating the navigation instrument so that the bent tip is pointed into and subsequently advanced into the bronchial branch of interest. In one embodiment, as the tracked navigation instrument is advanced towards the target, the catheter is advanced along or behind the tracked instrument.

The tracked navigation instrument is advanced until it is adjacent to the target. At that point, the catheter is advanced until it too is adjacent to the target. Then, the tracked navigation instrument may be withdrawn, leaving the empty catheter. The catheter is now in position for delivery of instrumentation such as a biopsy devices, brushes, lavage equipment, or other instruments. These instruments can be inserted into the catheter and guided directly to the target. While it may be helpful, there is no need to track the instrument, since the catheter is ideally be positioned immediately adjacent to the target.

Other methods of navigating to the target may be used. For example, the catheter itself may be tracked using a tracking system and one or more position indicating elements. In one embodiment, the tracked catheter may be steerable or have a bent tip for navigation through the lung to the target, similar to the navigation of the tracked navigation instrument. An instrument may then be slid down the tracked catheter to perform a procedure on or near the target.

Still another method for navigating an instrument to a target in the lung involves a tracked instrument, which may be navigated to the target similar to the navigation of the tracked navigation instrument.

The various objects, features, and advantages of the invention will be apparent through the detailed description of the preferred embodiments and the drawings attached hereto. It is also to be understood that the following detailed description is exemplary and not restrictive of the scope of the invention.

BRIEF DESCRIPTION OF THE DRAWINGS

FIGS. 3A and 3B illustrate a section of a lumen equipped with position indicating elements according to an embodiment of the invention.

FIGS. 3C and 3D illustrate a section of a bronchoscope equipped with position indicating elements according to an embodiment of the invention.

FIGS. 10A-10C illustrate methods for navigating an instrument to a target in the lung according to embodiments of the invention.

DETAILED DESCRIPTION OF PREFERRED EMBODIMENTS

The invention provides methods and apparatus for guiding an instrument to a target in the lung. In one embodiment, an apparatus for guiding an instrument to a target in lung may include a bronchoscope with a working channel, an instrument for performing a procedure, a tracked navigation instrument equipped with at least one trackable position indicating element, a catheter or other hollow lumen serving as an extension or replacement of the bronchoscope or the bronchoscope's working channel, one or more motion compensation devices, or other devices or elements. The apparatus may utilize a combination of some or all of the above devices to guide an instrument to a target in the lung and perform image-guided pulmonary treatment, investigation, or examination.

Figure 1:
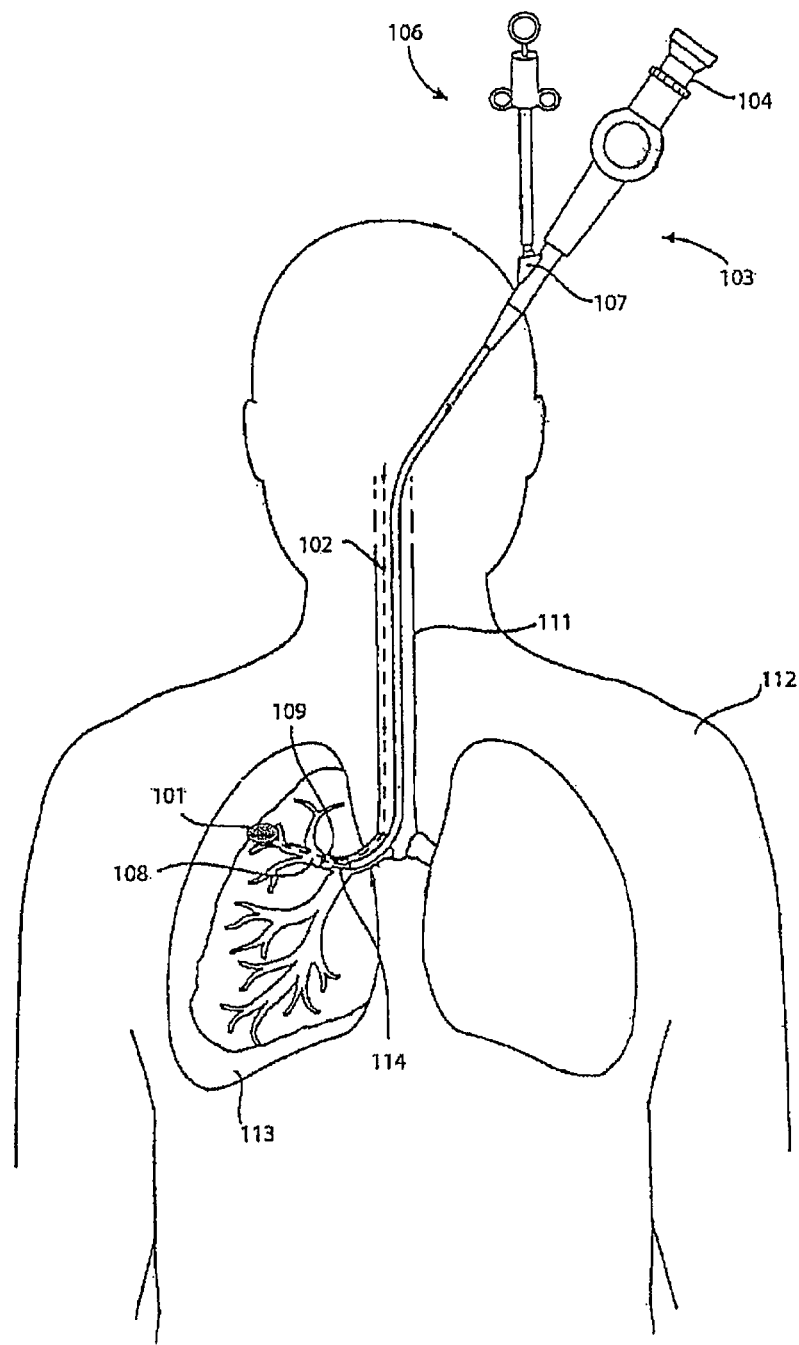
FIG. 1 illustrates a bronchoscope that is utilized to navigate to a target in the lung.

The bronchoscope used in the apparatus of the invention may be the same as or similar to bronchoscopes known in the art such as, for example, bronchoscope 103 described in FIG. 1. The instrument for performing a procedure (e.g., medical instrument) may include a catheter, a needle, a biopsy device, a brush, a laser, a grasping device, an irrigation device, a radio frequency (RF) ablation device, a bronchoscope, an ultrasound probe, or other devices compatible with bronchoscope based examination, investigation or therapy. Typically, these devices are placed into the working channel of the bronchoscope. They may optionally contain position indicating elements.

As used herein, position indicating elements refers to an element or sensor whose location, position, orientation, and/or coordinates relative to a tracking device may be determined and recorded. A position indicating element may include, for example, a coil that may produce a magnetic field that is detectable by an electromagnetic tracking device. Other types of position indicating elements and/or tracking devices may be used. One of ordinary skill in the art will realize that any process, method, apparatus, system, or feature described herein that utilizes one or more position indicating elements may be assumed to also utilize a corresponding tracking system and any associated computer equipment necessary to facilitate the use thereof within the invention.

Figure 2:
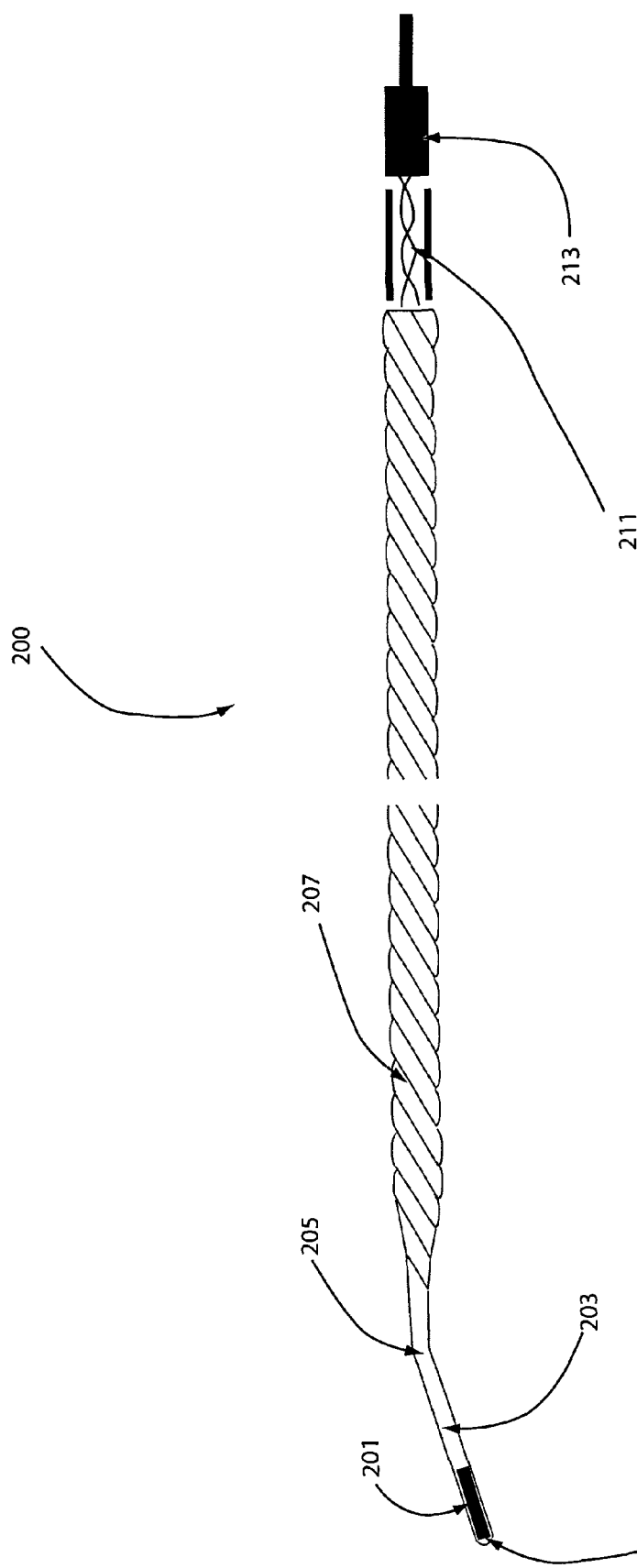
FIG. 2 illustrates a tracked guidewire that may be used as a tracked navigation instrument according to an embodiment of the invention.

FIG. 2 illustrates an electromagnetically tracked guidewire 200 that may be utilized as a tracked navigation instrument according to an embodiment of the invention. Other instruments or tools may be used a tracked navigation instruments in accordance with the invention such as, for example, a catheter, a needle, a biopsy device, a brush, a laser, a grasping device, an irrigation device, a radio frequency ablation device, a bronchoscope, an ultrasound probe, or other tool or device.

Guidewire 200 may include a position indicating element 201 at or near its tip 203. In some embodiments, guidewire 200 may include lead wires 211 extending from position indicating element 201 to electrical connections 213. Electrical connections 213 may facilitate measurement of the position of position indicating element 201 and the connection of guidewire 200 to a tracking system and/or other computer-implemented system. In some embodiments, guidewire 200 may include a bend 205 near tip 203. Bend 205 may be a 20-45 degree bend and may be coated with a lubricious coating 207 (as may be the remainder of guidewire 200). Other bend geometries including tips without bends and/or bends of other magnitudes may be used. Malleable tips that can be custom bent as required by a surgeon may also be used. Tip 203 may be tapered or of reduced diameter so as not to be as stiff as the shaft of the wire and/or may and have a rounded end 209 so as not to cause excessive trauma to the bronchial path though which it is navigated.

The dimensions of guidewire 200 may be such that it can fit and is slidable and rotate-able within the working channel of the bronchoscope (e.g., bronchoscope 103), a lumen (e.g., tube 300 described below), or within other environments. For example, in some embodiments, the dimensions of the guidewire may be between 0.3 and 2.1 mm in diameter, depending on the diameter of the bronchoscope's working channel and the diameter of the bronchial tubes that are to be navigated. In general, the dimensions of guidewire 200 may be as small as possible to permit the navigation discussed herein and to accommodate an accurate sensor. The length of the guidewire 200 may be several centimeters longer than bronchoscope 103 or other bronchoscope with which guidewire 200 is to be used. The stiffness of the guidewire 200 may be such that it is stiff enough to pass through any mucous that may be encountered in the lung. The torque transfer properties of guidewire 200 may be such that 1 proximal revolution of the wire shaft turns uniformly to 1 revolution of the tip over all increments of motion. For example, in one embodiment, a design containing a multifilar bundle such as that shown in FIG. 2 may accomplish such a torque transfer. However, other designs available in the field of intravascular guidewire fabrication may be used. In some embodiments, guidewire 200 may be steerable using a proximally located steering mechanism. Such mechanisms are known in the art for steering intravascular guidewires and catheters.

In some embodiments, guidewire 200 may include more than one position indicating element. If guidewire 200 contains two or more position indicating elements, at least one may be contained within a deflecting portion of tip 203 and one within the main body of guidewire 200. This way it will be possible to determine the angle of tip 203 relative to the rest of guidewire 200 (which provides additional information relative to the patient's anatomy and guidewire 200's position in the patient's anatomy).

As mentioned above, the apparatus for guiding an instrument to a target in the lung may include a catheter or other hollow lumen (herein referred to as the "catheter") that may serve as an extension of the working channel of a bronchoscope (e.g., working channel 106 of bronchoscope 103) or completely supplant the bronchoscope. The catheter is constructed such that it can contain tracked guidewire 200. This is accomplished by the catheter containing at least one lumen through which the guidewire may be slidably coupled. The outer diameter of the catheter may be small enough to fit inside the working channel of the bronchoscope and may be smaller than a tracked working channel liner for bronchoscope (if such a liner is used). However, the inner diameter of the catheter may large enough to accommodate tracked guidewire 200 and any medical instrument that will be inserted into it. Guidewire 200 may be slidable within the catheter or other passageway in which it is used. The catheter's mechanical properties may enable it to follow the guidewire. For example, in one embodiment, the catheter may accomplish this by having a bending stiffness that is as close as possible to the bending stiffness of guidewire 200 (especially at its tip). The interior lumen of the catheter that contains guidewire 200 may also be highly lubricious so that the guidewire is slidable with very low friction. This may be accomplished by the use of a Teflon™ lumen or other highly lubricious material coating wither the interior of the catheter, the exterior of guidewire 200, or both. The catheter may also have good "pushability" and not compress or buckle when pushed.

In one embodiment, the catheter may be used to perform initial navigation into the lung and may contain position indicating elements. In this embodiment, the catheter itself may contain a pre-bent end to assist in the navigation and may have many of the other properties discussed of guidewire 200 above.

In one embodiment, the apparatus for guiding an instrument to a target in the lung may include one or more dynamic referencing devices. In some embodiments, some or all of the one or more dynamic referencing devices may each comprise a separate lumen that is inserted into a different location of the lung (e.g., a different bronchial branch from the bronchoscope) or is inserted elsewhere in the body (e.g. the blood vessels). In some embodiments, the location into which a dynamic referencing device is inserted may be proximal to a target area. In other embodiments, the location into which a dynamic referencing device is inserted may not necessarily be proximal to the target area, but may be a location that will provide adequate sampling of patient motion so as to preserve a registration of the desired parts of the patient's anatomy. In one embodiment, the one or more dynamic referencing devices may each be equipped with one or more position indicating elements.

FIGS. 3A and 3B illustrate a section a tube 300 (FIG. 3B illustrating a cross-section of tube 300 at sec. A) which may be a bronchoscope, a tube such as a catheter, or other device including an interior lumen, that may be inserted within the working channel of the bronchoscope or a completely separate tube that may be inserted directly into a lung. According to an embodiment of the invention, tube 300 may comprise or be included in a dynamic referencing device of the invention or may serve as a multipurpose device, one function of which is to perform dynamic referencing. Tube 300 may include one or more position indicating elements 301. In some embodiments, position indicating elements 301 may be placed in a catheter 303 that is located or placed within tube 300. In some embodiments, catheter 303 is housed within a main passageway 305 of tube 300. In one embodiment, a tool or guidewire can also be slideably inserted into main passageway 305 of tube 300. In an embodiment, this tool or guidewire can be used to assist in navigating tube 300, to assist in dynamic referencing, to verify registration or a number of other uses. In one embodiment, tube 300 may include a second passageway 307 within main passageway 305, in which a tool or guidewire may be inserted.

As mentioned above, lumens acting as dynamic referencing devices such as, for example, tube 300 may be inserted through a separate bronchial pathway so as not to interfere with the procedure involving the bronchoscope. In some embodiments, tube 300 may be inserted "freehand" or through the bronchoscope. In an embodiment, wherein tube 300 is inserted through the bronchoscope, the bronchoscope may be removed by sliding over tube 300, leaving tube 300 in place. In some embodiments, tube 300 need not be removed from the bronchoscope if the bronchoscope is used to position tube 300. Instead, an extended working channel or tracked instrument may be inserted through the bronchoscope and through lumen 307 for example, while position indicating elements 301 perform dynamic referencing tasks.

In some embodiments, the exact pathway of tube 300 need not follow a specific route in the lung, except to say that the location should be close to the location of intervention, ideally in the same lobe of the lung. When used as a dynamic reference, tube 300 should not move within its environment once placed and one or more implements such as, for example, hooks, balloons, cages, wires, or other implements may be used to secure it.

In one embodiment, some or all of the one or more dynamic referencing devices may include a surface mounted reference. In one embodiment, a surface mounted reference may be attached to the chest in the form of one or more position indicating elements sensors the form of, for example, a patch that is stuck onto the chest with adhesive. Once placed, the surface patch should not move relative to the body part to which it is attached, but may move in a manner indicative of the patient's motion. An example of a skin patch that may be used as part of the present invention is the skin patch described in U.S. patent application Ser. No. 11/271,899 by Glossop, entitled "Integrated Skin-Mounted Multifunction Device for use in Image-Guided Surgery," (U.S. Patent Application Publication No. 20060173269) which is hereby incorporated herein by reference in its entirety. As demonstrated by U.S. patent application Ser. No. 11/271,899, additional features may be present on the surface patch.

As mentioned above, in one embodiment, a bronchoscope may be directly tracked and utilized as a dynamic referencing device by incorporating position indicating elements serving as dynamic referencing devices into or onto the bronchoscope or by integrating position indicating elements into lumens secured in the scope. These position indicating elements may also enable tracking and navigation of the bronchoscope to a target in the lung. FIGS. 3C and 3D illustrate a section of a tracked bronchoscope 351 according to an embodiment of the invention (FIG. 3D illustrating a cross-section of bronchoscope 351 at sec. B). The main tube 353 of bronchoscope 351 may be outfitted with fixated position indicating elements 355. In the embodiment illustrated in FIGS. 3C and 3D, two position indicating elements 355 (additional position indicating elements may be used) are attached externally to bronchoscope 351 via a sleeve 357 fitted over bronchoscope 351 using, for example, a combination of shrink-tube and/or adhesive (this leaves an un-obstructed interior channel in bronchoscope 351 for passage of wires or instruments). Another method of tracking a bronchoscope may include altering the construction of the bronchoscope to facilitate embedding the sensors directly. Still another method of tracking the bronchoscope may include creating a tracked working channel liner in which a separate interior lumen, such as catheter 303 of FIGS. 3A and 3B, is inserted and secured in the working channel of the bronchoscope. Other methods of securing position indicating elements 355 to bronchoscope 351 so that it can serve as a dynamic referencing device or otherwise be tracked may also be used.

Other implements may be employed in conjunction with dynamic referencing of a patient's anatomy in accordance with embodiments of the invention. For example, "rib tracking" involves attachment of a position indicating elements directly to a rib close to the region of intervention. These position indicating elements may take the form of one or more tracked bone screws or K-wires. Additionally, screws or wires may be used to attach a separate tracked dynamic referencing device to one or more ribs. An example of a K-wire equipped with a position indicating element can be found in U.S. patent application Ser. No. 11/333,364, by Glossop, entitled "Electromagnetically Tracked K-Wire Device", which is filed concurrently herewith (U.S. Patent Application Publication No. 20060173291) and which is hereby incorporated by reference herein in its entirety.

Another method of dynamic referencing may use one or more needles containing integrated position indicating elements that are inserted into the chest. Fine gauge needles may even be employed that enter the lung directly. Alternatively the tracked needles may be lodged in an intercostals space. An example of these devices may be found in U.S. Pat. No. 6,785,571, to Glossop, entitled "Device and Method for Registering a Position Sensor in an Anatomical Body," and U.S. Provisional Patent Application No. 60/626,422, by Glossop, entitled "Device and Method for Registering and Dynamically Referencing Soft Tissue for Image Guided Surgery," both of which are hereby incorporated by reference herein in their entirety.

In some embodiments, physiological state indicators may be used as an alternative to or in addition to dynamic referencing. Physiological state indicators enable synchronizing ("gating") the acquisition of position/orientation information to the physiological motion (e.g., heartbeat, respiration, or other repeated or cyclical motion) of the patient's anatomy. For example, when a signal indicating a particular part of the respiratory cycle is received, the image-guided system is instructed to begin acquiring valid position/orientation data regarding the position indicating elements included in the instruments being employed for the procedure. Once the respiratory cycle moves outside of that phase, a "stop" signal is issued to halt the data collection. In this way, it is not necessary to track the motion of the patient's anatomy if the respiratory motion is the only motion occurring. As mentioned above, physiological state gating may be used in place of or in conjunction with dynamic referencing and may increase the accuracy of the system.

In one embodiment, gating may be facilitated by a trigger point identified for the motion being gated (e.g., respiration).

The trigger point on a respiration machine (if used) may generate a signal indicating a certain phase of the respiratory cycle that is then used to trigger gating of data acquisition. The signal generated by the respirator may be native to the respirator or may be used in conjunction with a sensor applied to the respirator.

In other embodiments, gating may employ a measurement device that is applied to the patient to determine the respiratory (or other) cycle. The physiological state indicating device may include, for example, a pressure sensor, a chest expansion sensor, spirometer, an Electromyographic device, a breath temperature sensor, an oxygen sensor, a carbon dioxide sensor, a signal from a respirator, an extensometer, an electrocardiograph, a cardiac gating device, devices that analyze the gas composition of the exhaled breath, or other such measurement device.

Figure 4:
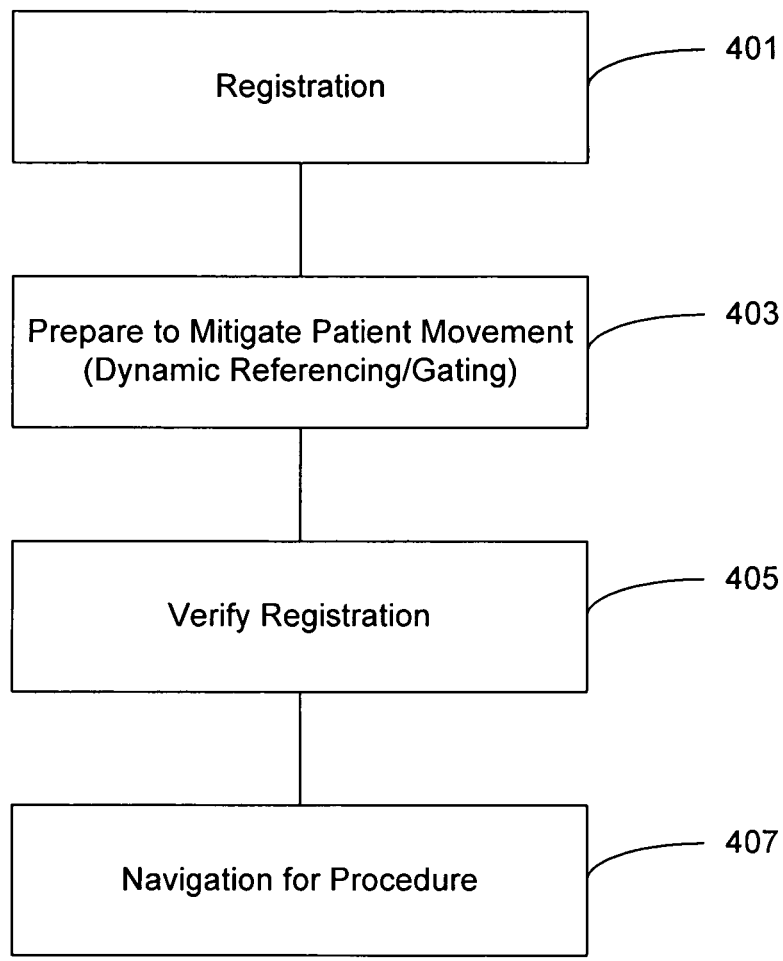
FIG. 4 illustrates a process for navigating an instrument to a target in the lung according to an embodiment of the invention.

In one embodiment, the invention provides a method for guiding an instrument to a target in the lung of a patient. FIG. 4 illustrates a process 400 according to an embodiment of the invention, wherein a lumen is guided to a target in the lung. In one embodiment, some or all of the operations of process 400 may be performed using the instrumentation and apparatus discussed herein. In an operation 401, registration of the patient may be performed.

Figure 5:
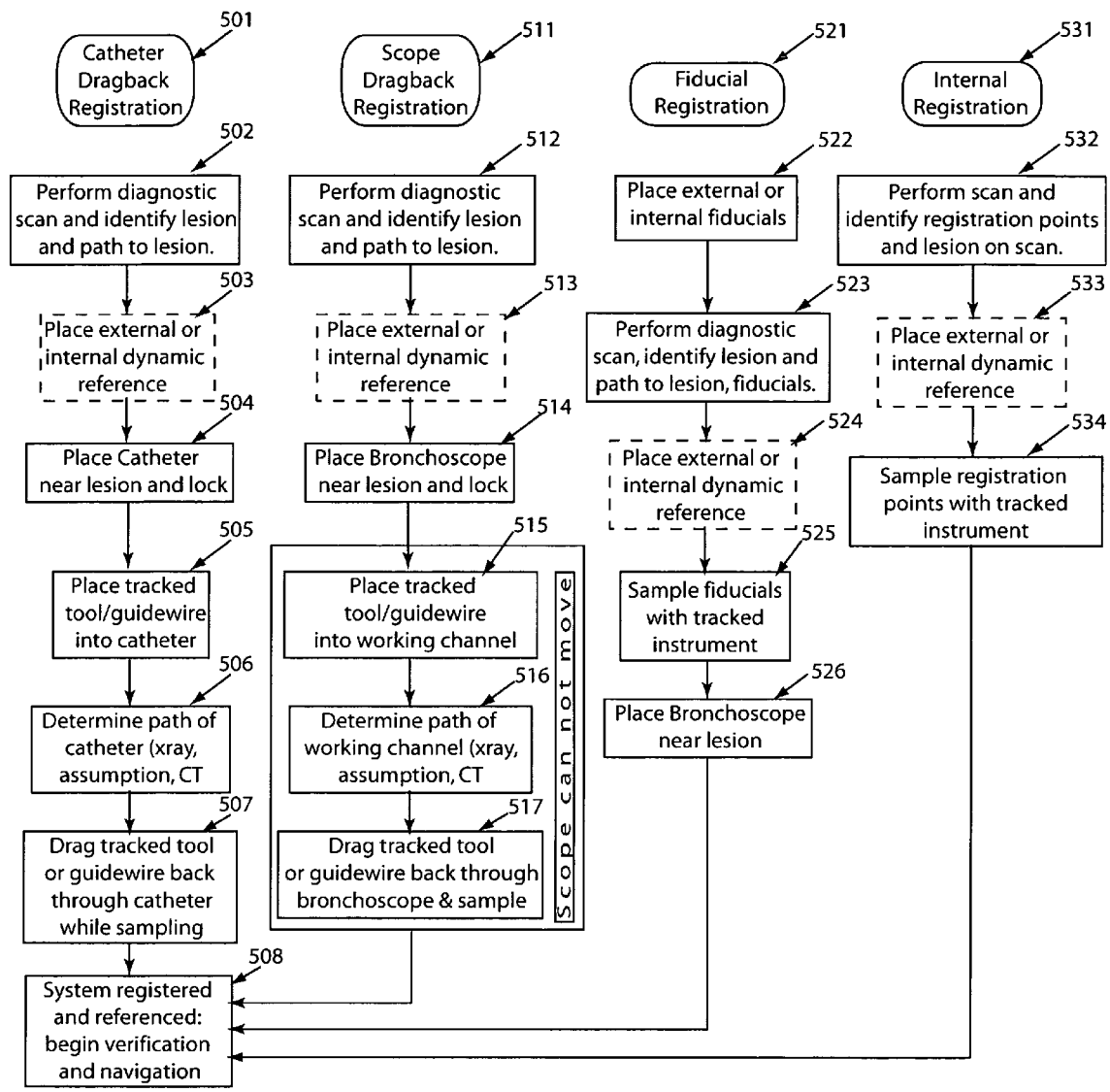
FIG. 5 illustrates methods for registering a patient's anatomy according to an embodiment of the invention.

As mentioned above, registration is the process whereby the image space coordinates are brought into alignment with patient space coordinates. Registration may be performed by several techniques. Techniques and associated devices for registration are described in U.S. Pat. No. 6,785,571, to Glossop; U.S. patent application Ser. No. 11/059,336 (published as U.S. Patent Publication No. 20050182319) by Glossop; and U.S. patent application Ser. No. 11/271,899, by Glossop, each of which is hereby incorporated by reference herein in its entirety. FIG. 5 illustrates four registration methods 501, 511, 521, and 531, any of which may be used to register the anatomy of the patient. Other methods may also be used.

Method 501 illustrates registration using "catheter dragback." In an operation 502, a diagnostic scan is first obtained and some planning operations performed. In an operation 503, a dynamic referencing device may optionally be placed. The dynamic referencing device, if used, may be incorporated in a catheter used for the registration or may be a separate device such as, for example, a tracked lumen, an external skin patch, or other dynamic referencing device. Although not explicitly shown, the dynamic referencing device may also incorporate a gating device.

In an operation 504, the catheter is inserted into a vessel, bronchial pathway or other location within the patient close in proximity to a target (e.g., a lesion, mass, tumor, or other area of interest) and locked in placed using balloons, hooks, or other device or by simply lodging it in place. The exact location of the catheter is not necessarily important except that it should be located near enough to the target and surrounding area that it can be assumed to move together with the target as a rigid body. The catheter could also be a hollow, preferably curved, needle that is inserted into adjacent tissue percutaneously. In some embodiments, the catheter may also include or be replaced by any natural or artificially created conduit in the body.

In an operation 505, a tracked tool or guidewire (equipped with one or more position indicating elements) is inserted into the catheter. In an operation 506, the 3D pathway of the catheter is determined by assumption of the pathway (e.g., from a priori knowledge of the path combined with knowledge that the catheter is in this path and is likely to have undergone certain modifications to the path), by direct imaging (e.g., by CT scan, by fluoroscopic views, or other imaging modality). This 3D pathway provides the 3D "image space" coordinates of the registration path.

In an operation 507, the tracked tool or guidewire in the catheter is dragged or moved back or forward through the catheter or other conduit. A locus of points is obtained in the "patient space" by sampling the position of the one or more position indicating elements on the wire as the wire is dragged back through the catheter. Once gathered, these points are mathematically combined with the image space points to obtain the registration matrix relating the image space and patient space. Techniques for performing the registration calculation are well known and include, for example, the iterative closest points (ICP) method or other techniques.

Once registered, the system is verified in an operation 508 to ensure it is accurate. If it is shown to be accurate, then the navigated intervention involving the target can begin.

Figure 6:
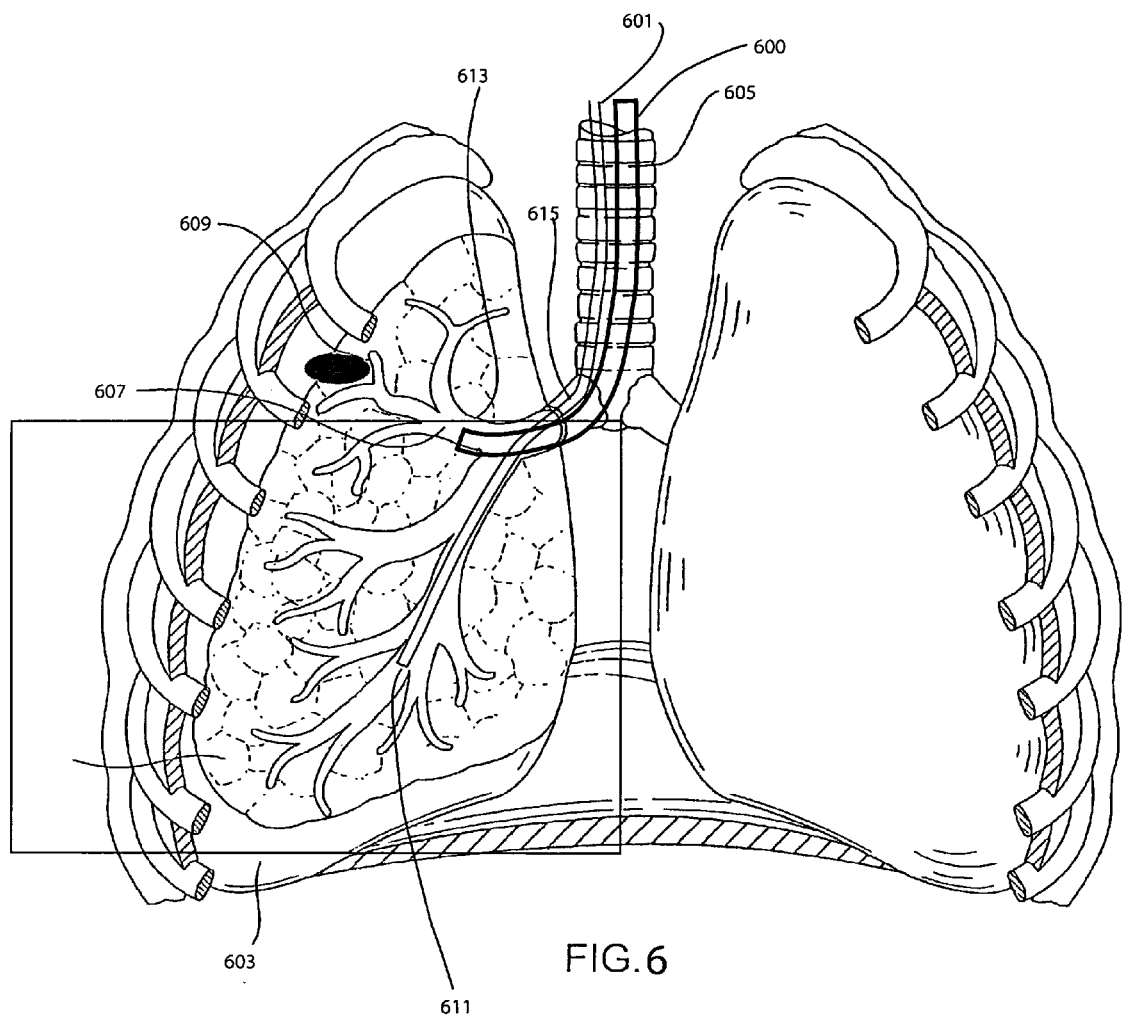
FIG. 6 illustrates the use of apparatus in performing a registration according to an embodiment of the invention.
Figure 7A:
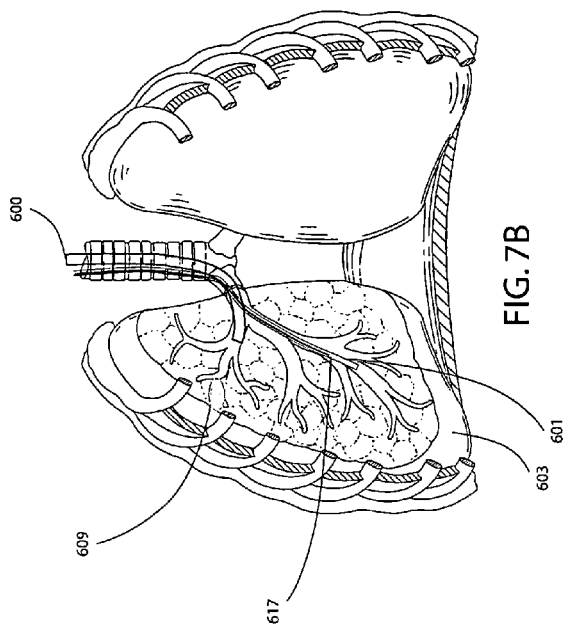
FIGS. 7A-7D illustrate the use of apparatus in performing a registration according to an embodiment of the invention.
Figure 7B:
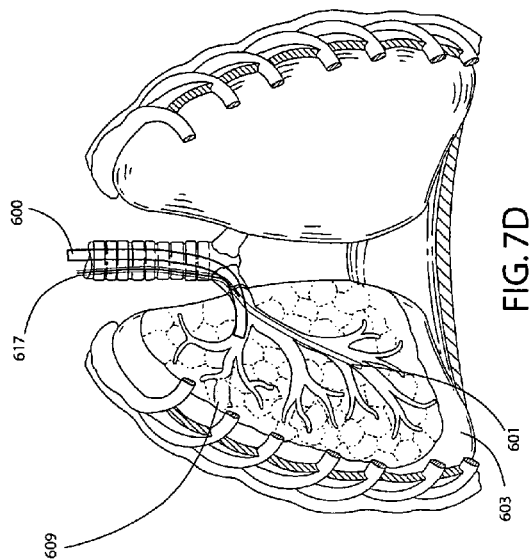
Figure 7C:
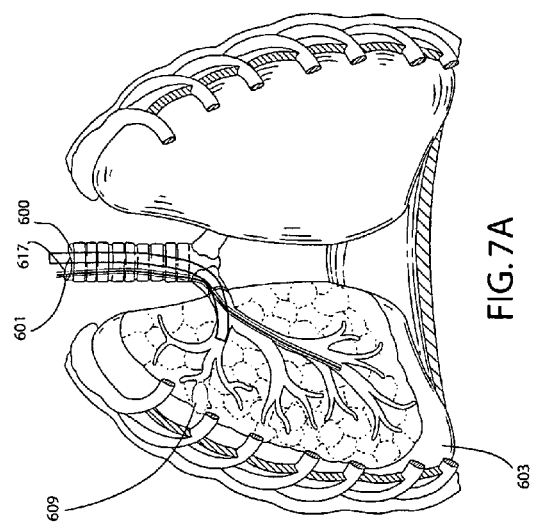
Figure 7D:
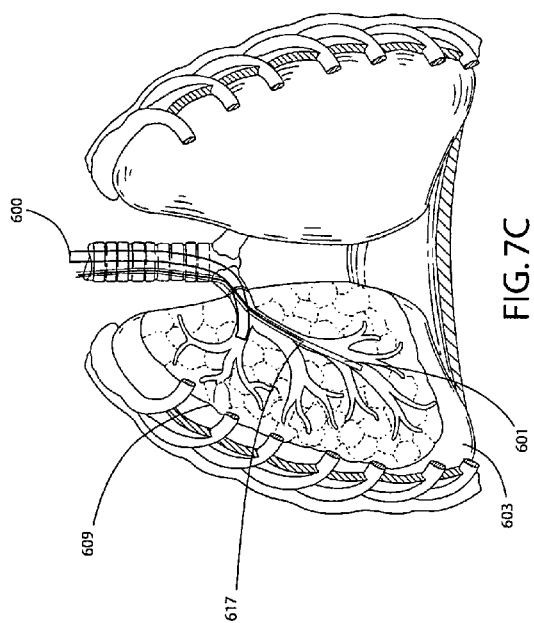

FIG. 6 illustrates the use of certain apparatus of the invention to perform a registration (e.g., method 501) according to an embodiment of the invention. In FIG. 6, a bronchoscope 600 and a registration catheter 601 are shown inserted into lung 603 via the trachea 605. Bronchoscope 600 is shown in a branch 607 of lung 603 close to target 609 (e.g., which may be a lesion, mass, tumor, or other item of interest). Catheter 601 is lodged into a branch of the bronchial tree near but not necessarily adjacent to target 609. The tip 611 of catheter 601 is located in a branch of the bronchial tree that does not interfere with target 609, bronchoscope 600, or tip 613 of bronchoscope 600 (tools may be extended from tip 613 of bronchoscope 600 to access target 609). In general it is best to have as many inflection or bend points such as 615 in catheter 601 as possible to increase the fidelity of the registration. The various components may then be used for registration of the patient's anatomy according to method 501 (or by another method). Catheter 601 may then be removed. Alternatively it can remain in place if it is being used as a dynamic reference or if it is anticipated that it may be needed to re-register the patient's anatomy at some later time in the procedure.

One embodiment of the dragback technique using a catheter is illustrated in FIGS. 7A-7D. FIGS. 7A-7D illustrate catheter 601, tracked guidewire 617 (having one or more position indicating elements) inside the lumen of catheter 601, and bronchoscope 600 (all within lung 603). During dragback, tracked guidewire 617 is removed from catheter 601 (which can be seen in FIGS. 7B-7D) while acquiring data points along the path (e.g., by sampling the position of the position indicating elements of the tracked guidewire).

An alternate version of the dragback registration includes "scope-dragback." FIG. 5 illustrates a flow chart of "scope dragback" in method 511. In an operation 512, a scan is performed and the target, path to the lesion, and other salient features are identified from the scan. In an operation 513, a dynamic referencing device may then be placed (if desired). In an operation 514, the bronchoscope is placed into the lung near the target and locked in position so that it does not move. This can be accomplished by fixing the steering mechanism of the bronchoscope or by inflating balloon cuffs so that the bronchoscope does not move. The bronchoscope must then remain in the fixed position for the duration of the intervention.

The registration is performed in a manner similar to the previously described dragback technique. However, instead of inserting a tracked guidewire into a catheter, the tracked guidewire (or other tracked tool or instrument) is inserted into the bronchoscope's working channel in an operation 515. In an operation 516, the path of the working channel is determined in image space using an imaging modality. In an operation 517, the patient space data is obtained by dragging the tracked guidewire back through the bronchoscope's working channel while sampling its location (e.g., using the position of the position indicating elements in the tracked guidewire) in patient space. A registration matrix is then calculated and verification may proceed as indicated in operation 508.

In the case where a bronchoscope is not used, the lumen or catheter may be placed freehand or by another method and the dragback method applied as described above.

Additional registration methods may also exist such as, for example, fiducial registration of method 521. Fiducial registration uses pre-applied fiducial markings placed on the patient's skin or placed internally in an operation 522. In an operation 523, a scan is performed using an imaging modality, and the target, the path to the target, and the fiducials are identified. In an operation 524, a dynamic referencing device may be placed in or on the patient's anatomy (if used). In an operation 525, the position of the fiducials are sampled in patient space using a tracked probe or pointing device. Once the registration is complete, the bronchoscope (which can be tracked or untracked) is placed near the target in an operation 526.

Multiple possible variations of the applied fiducials may be used. For example, a fiducial that may produce high quality position information in image space may include a small ball bearing that is taped to the skin. Equally, a fiducial can be applied internally such as a "seed" or other form placed using a needle or other technique. A fiducial may also be temporarily inserted in or on adjacent tissue (e.g., a bone screw or k-wire screwed into a rib). Multiple fiducials may be applied and used as a single unit (e.g., a surface patch could be applied that contains 3 or more fiducials). Equally, a needle or catheter could be applied internally (e.g. into the lung structure, poked into the skin or tissue) or externally (e.g. taped onto the surface) that contains one or more of fiducial markers.

Another method of registration that may be used with the invention is internal bronchial registration, represented by method 531. Internal bronchial registration has been previously reported by Solomon et al. (S. Solomon et al., *Three-dimensional CT-Guided Bronchoscopy With a Real-Time Electromagnetic Position Sensor: A comparison of Two Image Registration Methods*, Chest, 118, 6, December 2000, at page 1783). In an operation, 532, a diagnostic scan is performed using an imaging modality and the paths, the target, and numerous registration features (e.g., naturally occurring features or "natural fiducials") are identified in the image space of the scan. In an operation, 533, a dynamic referencing device is positioned (if used). In an operation 534, patient space sampling of the registration points is accomplished by placing the bronchoscope in the vicinity of each of the registration features previously identified in the image space of the scan, and probing the feature with a tracked instrument such as a tracked guidewire inserted into the bronchoscope. Such natural fiducials include bifurcation points, identifiable nodules, or other natural features of the patient's anatomy.

Still another registration method (not illustrated in FIG. 5) uses the concept of "surface matching". This method is also known in the art and involves specification of a match surface. The surface must be segmented out of a scan if the patient in some manner so that a mathematical representation of the surface is available. The surface may be represented as a point cloud, a two dimensional spline, a triangularized mesh, a voxel set or similar representation for example. The patient space coordinates are obtained by random or systematic touching of numerous points on the surface, forming a point cloud. The point cloud is matched with the image space coordinates using methods known in the art such as the ICP (Iterative closest point) algorithms.

Other methods of registration may exist or may be fabricated by combining one or more of the other techniques. For example, point based combined with surface matching; applied fiducial combined with intrinsic fiducials; path registration combined with fiducial based; or other methods or combinations.

Additionally, it is possible to perform navigation without the use of explicit registration. Methods for doing this are disclosed in U.S. patent application Ser. No. 11/271,899, by Glossop, which discusses, inter alia, a method for placing a target over the location of a lesion and steering a bronchoscope or catheter to a location directly below the target to offset by some predetermined amount from it.

Referring back to FIG. 4, once the patient's anatomy has been registered in operation 401, process 400 for guiding an instrument to a target in the lung may proceed to an operation 403, wherein preparations may be made for the compensation for/mitigation of patient movement during subsequent navigation or procedures (e.g., dynamic referencing and/or gating).

Relative motion between the patient and a position indicating element in a tracked instrument can seriously degrade any registration that has occurred or that is in the process of occurring. Patient motion can result from normal respiration, coughing, spasm, accidental movement of a position indicating element, or a host of other possible sources. There are several ways to mitigate patient motion. Some of these methods and associated devices are discussed in U.S. Pat. No. 6,785,571; U.S. patent application Ser. No. 11/059,336; and U.S. patent application Ser. No. 11/271,899, each of which is hereby incorporated by reference herein in its entirety.

One method of mitigating patient motion is gating through physiological state monitoring. As discussed previously, gating is a method of taking data samples at the same point in a repeating cycle. Preferably, the registration to be used in the procedure is performed at the same point in the repeated cycle (e.g., respiratory cycle) as the original scan or dynamic reference used. For example, this can be done for example during the peak inspiration or expiration phase of respiration as determined either manually (through observation of the respirator or patient), through an electronic feedback signal from the respirator, or through a signal from an electronic monitor such as a pressure or position based respiration sensor. In another form of gating, data measurements are suppressed until the same point in the cycle is detected. In still another form of gating, the patient or an external device imposes the state e.g. by holding the breath or by causing breathing to cease temporarily and maintaining that state during the data measurement. In the context of the invention, the data measurement may refer to the sampling of the position of one or more position indicating elements of a tracked tool being used for a procedure in the lung.

An alternative to, or in addition to, gating is dynamic referencing. In dynamic referencing, a dynamic referencing device (see those described above) is applied to the patient (either prior to or after registration) and used to compensate for chest and heart motion and/or various other patient motions in the region of interest. In some embodiments, the dynamic referencing device takes the form of a "dynamic referencing insert", such as a sleeve containing one or more position indicating elements that is placed into the working channel of a bronchoscope or endoscope. A dynamic referencing device can also be incorporated into a bronchoscope directly. Furthermore, a dynamic referencing device may also comprise or be placed inside a separate device such as a cannula, a catheter, a lumen, or other device that is introduced into a portion of the lung or blood vessel near the intervention site.

In one embodiment, dynamic referencing can be performed using a surface tracker such as a skin patch or other surface device. The surface tracker may be applied to the patient prior to registration.

As previously mentioned, gating can be used in combination with dynamic referencing to further improve results. This is especially useful in obtaining data at the same point as the scan was obtained. This can be done with combination devices such as for example, bronchoscopes that measure pressure and position.

After preparation for mitigation of patient movement, process 400 may continue to an operation 405 for verification of registration fidelity. A verification operation should be performed to ensure that the system has been adequately registered, is being correctly gated or dynamically referenced, and is otherwise sufficiently accurate to enable a procedure to be performed with confidence. There are several ways to verify registration. Some of these methods and associated devices are discussed in patent application Ser. No. 11/059,336; and U.S. patent application Ser. No. 11/271,899, each of which are hereby incorporated by reference herein in their entirety.

In some embodiments, verification relies on performing a registration and then manipulating a tracked instrument near the point that the intervention will be occurring. In one embodiment, a tracked device is used to touch a known location such as, for example, a feature on the patient or a fiducial applied to the patient. The registration is used to produce a reconstructed graphical icon representing the tip of the probe. This icon is examined see if it is indicated to touch the proper location (e.g., the known location that was touched). This may be repeated for several locations to determine if the system appears to be accurate.

In another embodiment, verification may be performed by navigating a tracked device to an unknown location. An X-ray or CT may then be taken to examine the location of the tracked device, which is then compared to a graphical icon representing the tracked device as determined by the registration (which should, if the registration is accurate, indicate that the tracked device is touching the same location). This could be performed for example by creating a digitally reconstructed radiograph (DRR) that can be overlapped on the actual radiograph to quantify any error.

Likewise, path based verification can be performed. In path registration, a preferably tortuous pathway that has been imaged (e.g. a catheter or the working channel of the bronchoscope) is navigated with a tracked device. A reconstructed graphic icon of the tracked device (produced using the registration) is then viewed and compared to the image representation of the path. If the tracked device appears to be reasonably constrained to the image representation of the path over the length of traversal, then it can be assumed that the registration is accurate. As with path determination for the purpose of registration, the verification path can be obtained in image space using calibrated fluoroscopic measurements. If the verification path is segmented in image space, it is also possible to obtain a quantifiable indication of the accuracy of the verification by calculating the root mean square (RMS) differences between the two paths.

In a less informative extrapolation of verification, a path can be navigated by a tracked device along a constrained path within the anatomy of the patient and although the exact location of the navigating device is unknown, if it is found not to compromise the walls of the pathway as viewed on the images, then a necessary however not sufficient condition for accuracy has been demonstrated, although it will be highly likely that the registration is adequate.

Referring back to FIG. 4 and process 400, after the registration has been verified, navigation of an instrument may be performed within the anatomy of the patient for the purposes of conducting a diagnostic, interventional, or other medical procedure in an operation 407.

Figure 8A:
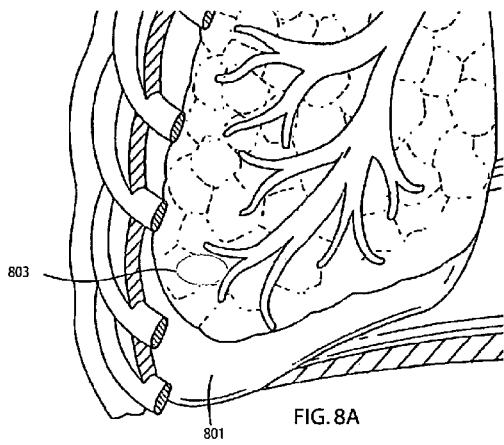
FIGS. 8A-8F illustrate the use of apparatus in navigating an instrument to a target in the lung according to an embodiment of the invention.
Figure 8B:
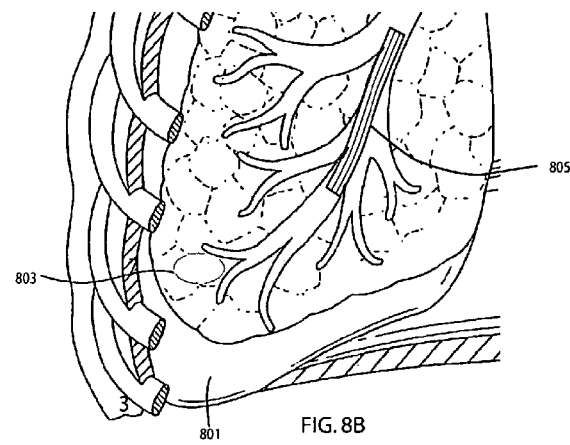

FIGS. 8A-8F illustrate a process for guiding an instrument to a target in the lung of a patient. FIG. 8A illustrates a target 803 in the lung 801 of the patient. FIG. 8B illustrates a bronchoscope 805 in lung 801 as close as possible to target 803. In some embodiments, navigating bronchoscope 805 to this point in the lung is done "freehand", as is commonly performed by experienced pulmonologists. With bronchoscope 805 so inserted, the patient's anatomy may then be dynamically referenced and verified according to one or more of the methods described in detail herein or according to another method. Dynamic referencing and/or verification may have been performed prior to insertion of bronchoscope 805; as such, it may not need to be done after bronchoscope insertion (or it may be done again). Alternatively, dynamic referencing and/or verification may not have been performed prior to bronchoscope insertion, in which case is may be done after.

Figure 8C:
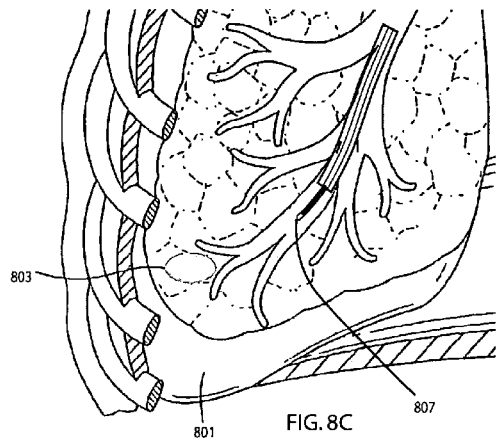
Figure 8D:
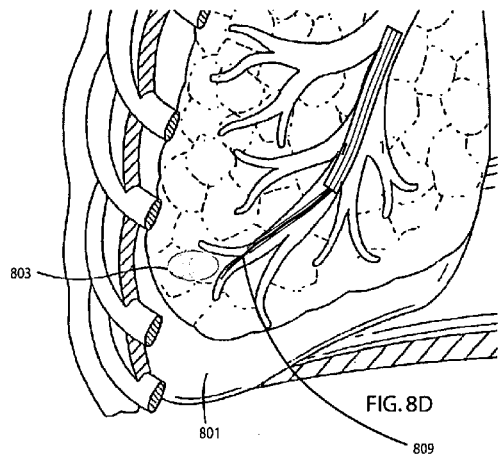

FIG. 8C illustrates a catheter 807 that is inserted into the working channel of bronchoscope 805 and navigated past the end of bronchoscope 805 further in lung 801 towards target 803. FIG. 8D illustrates a tracked guidewire 809 (the same as or similar to tracked guidewire 200 of FIG. 2) that is equipped with one or more position indicating elements (at least one being located at or near the tip of guidewire 809) which is inserted into catheter 807 and advanced toward target 803.

As the anatomy of the patient is registered and confirmed to be accurate, tracked guidewire 809 can be precisely navigated towards target 803 with navigational assistance from an image guided workstation (computer) that tracks and displays the position and/or orientation of the one or more position indicating elements of tracked guidewire 809. Similar to the above-described display of position indicating elements on images of patient anatomy with regard to registration and verification, tracked guidewire 809 (or indeed any tracked element or elements including one or more position indicating elements) may be superimposed onto one or more images of lung 801 and displayed by the workstation or other computer system. Target 803 may also be identified on the image of lung 801 and the position of tracked guidewire 809 relative to target 803 may be reflected on the displayed images as tracked guidewire 809 is moved through lung 801. As such, tracked guidewire 809 and its position on the displayed images aid in navigating the guidewire, and ultimately an instrument to tool, to target 803 in lung 801. In some embodiments, information regarding compensation for patient movement (e.g., dynamic referencing or gating information) may be used to compensate for patient movement in the displayed imaged (e.g., as a patient's anatomy moves, the motion compensation information is used to adjust the registration of the patient's anatomy and produce an accurate display of guidewire 809 in lung 801).

Figure 9A:
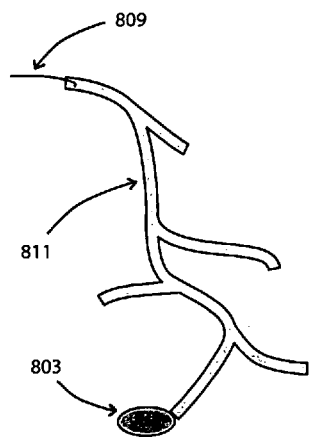
FIGS. 9A-9H illustrate navigation of a branched pathway using a bent tipped navigation instrument according to an embodiment of the invention.
Figure 9B:
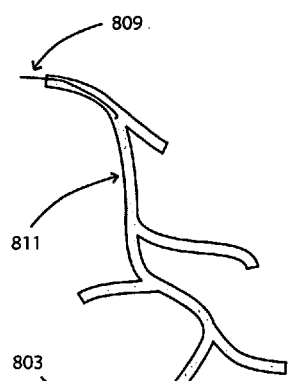
Figure 9C:
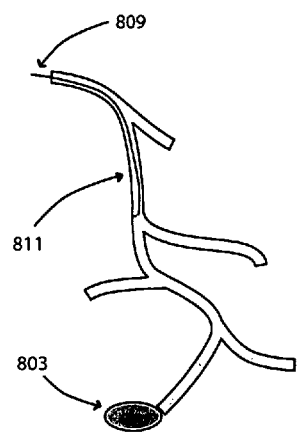
Figure 9D:
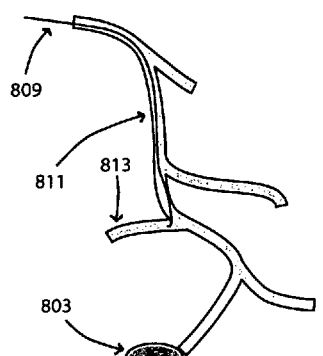
Figure 9E:
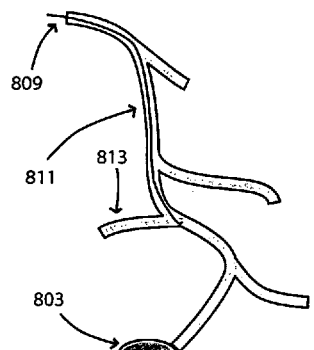
Figure 9F:
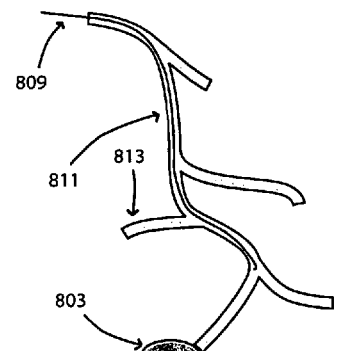
Figure 9G:
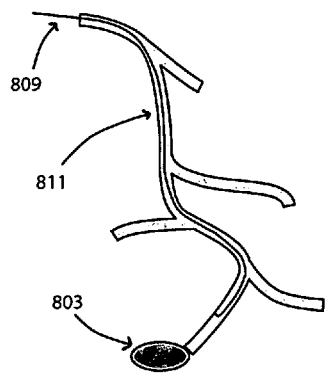
Figure 9H:
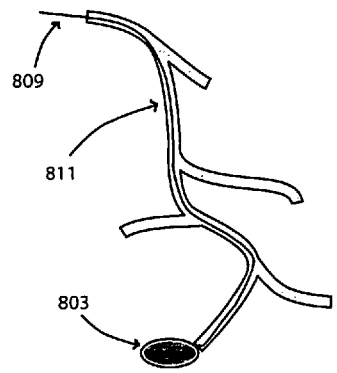

In some embodiments, as tracked guidewire 809 is advanced a little, catheter 807 may be advanced along with it. Tracked guidewire 809 may have a small bend (e.g., 20-45 degrees or other geometries) near the tip to facilitate this. The technique of advancing tracked guidewire 809 may proceed by identifying the intended path of the guidewire and navigating the path by carefully rotating the guidewire so that the leading bend of the wire is pointed into and subsequently advanced into the bronchial branch of interest. FIGS. 9A-9E illustrate utilizing a leading bend of a wire or instrument to navigate a through a branched or arboreal path. Such navigation is begun as guidewire 809 is advanced into a bronchial pathway 811 as illustrated in FIG. 9A. FIGS. 9B and 9C illustrate guidewire 809 being pushed downward, keeping the direction of the tip pointing in the direction of target 803. If the tip of guidewire 809 appears to be traveling in an undesirable side branch 813, as shown in FIG. 9D, guidewire 809 can be rotated (it has suitable torque conversion properties for such rotation) so that the bent tip points into a desired pathway, withdrawn from the errant path (side branch 813), and advanced toward target 803 as illustrated in FIGS. 9E and 9F. The process continues as shown in FIGS. 9G and 9H until guidewire 809 arrives at target 803.

The invention utilizes a refinement of this navigation process in that catheter 807 is advanced behind guidewire 809 as it achieves a correct direction (as indicated in FIGS. 8C and 8D). Catheter 807 constrains guidewire 809 and prevents it from buckling in the bronchial passageways and/or lodging itself. This occurs because the relatively tight fitting yet lubricious wall of catheter 807 reduces Euler buckling of the wire (except at the tip, which is not contained within catheter 807). Euler buckling occurs when a column such as a guidewire placed under axial load bends somewhere along its length and does not transmit axial force along its length. It reduces the ability of guidewire to be advanced.

Figure 8E:
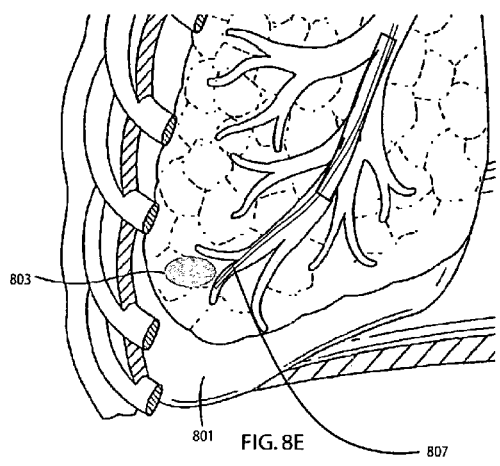

As mentioned above, catheter 807 is advanced behind guidewire 809 down to the proximity of target 803. In some embodiments, if a different guidewire with a different bend is required, guidewire 809 can be withdrawn from catheter 807 and replaced with one with the different bend or other feature. Guidewire 809 is advanced until it is adjacent to target 803 as shown in FIG. 8D. At that point, catheter 807 is advanced until it too is adjacent to target 803. Then, guidewire 809 can be withdrawn, leaving empty catheter 807, as illustrated in FIG. 8E. In some embodiments, immediately prior to treatment, the patient can be x-rayed, CT scanned, or otherwise imaged to confirm the position of catheter 807, if necessary.

Figure 8F:
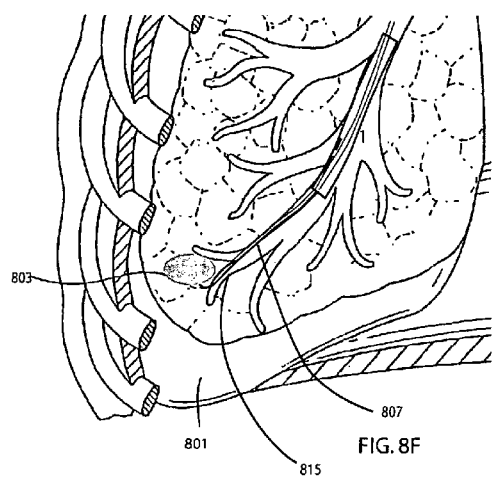

Catheter 807 is now in position for delivery of instrumentation such as a biopsy devices, brushes, lavage equipment, or other instruments. These instruments can be inserted into catheter 807 and guided to target 803. FIG. 8F illustrates a hook biopsy needle 815 that has been inserted into catheter 807. While it may be helpful to track the instrument, there is no need to do so, since catheter 807 will ideally be positioned immediately adjacent to the target. When the procedure is complete, everything is withdrawn through the bronchoscope.

FIG. 10A illustrates a flowchart of process 1001, wherein the navigation into lung includes a tracked guidewire (the same as or similar to the process illustrated in FIGS. 8A-8F. In an operation 1003, the tracked guidewire (e.g., guidewire 809) may be moved within the lung using the guidance of a tracking system that indicates the position of one or more position indicating elements on the tracked guidewire. In an operation 1005, a catheter (e.g., catheter 807) is slid behind the tracked guidewire until the guidewire and the catheter are adjacent to the target (e.g., target 803). An operation 1007 indicates that the guidewire may be withdrawn and replaced with one having different properties at any time during the navigation. In an operation 1009, the catheter may be secured within the lung using one or more of various methods known in the art (e.g., balloon, hook, or other methods). In an operation 1011, an instrument or tool may be slid down the catheter to perform a procedure. In one embodiment, a measurement may be taken to ensure that the tool protrudes from the catheter by a required distance that is necessary to perform the procedure.

Other methods of navigating to the target may be used. For example, FIG. 10B illustrates method 1031, wherein the catheter itself may be tracked using a tracking system and one or more position indicating elements. In one embodiment, the tracked catheter may have a bent tip and may utilize a tracked or untracked guidewire. The guidewire in this embodiment may be useful to advance the catheter, since it can be more easily manipulated than the catheter. In an operation 1033, the tracked catheter may be advanced in the lung to the target, making use of the bent tip (similar to the process illustrated in FIGS. 9A-9H). In an operation 1035, the tracked catheter may be followed by the guidewire (if one is utilized). In an operation 1037, the tracked catheter may be secured, similar to operation 1009 of FIG. 10A. In an operation 1039, an instrument may be slid down the tracked catheter to perform a procedure on or near the target, similar to operation 1011 of FIG. 10A.

FIG. 10C illustrates an additional method for navigating an instrument to a target in the lung 1061, wherein a tracked tool may be navigated to the target in an operation 1063. Although possible, this approach would require creation of tracked versions of a large number of preexisting devices and the likely high cost of such instruments may render it impractical.

Registration free methods may also be used to navigate instruments or lumens to a target. In this case, an external or internal tracking device placed in a known position relative to the target is steered toward using a tracked instrument. Once the tracked tool is within a threshold of the identified location, it is deemed to be at the target.

While the various systems, apparatus, methods, processes, and other features disclosed herein may be discussed in terms of electromagnetic tacking or position indicating elements that are electrically connected to an electromagnetic tracking system, it should be understood that the devices can be manufactured using passive magnetic or electromagnetic tracked sensors, optical fiber based sensors, GPS based systems, or other types of tracking system and position indicating elements or sensors.

While the invention disclosed refers to bronchoscopes and the lung, the identical principles may apply to endoscopes or similar equipment and any branched or unbranched lumens including blood vessels, digestive tracts, urinary tracts, ventricles, manufactured conduits placed within the body, or other parts of the anatomy.

Additionally, in some embodiments, some or all of the operations or steps of the methods, processes, or other features of the invention described herein may be performed in varying orders as would be appreciated by one having ordinary skill in the art. In some embodiments, additional operations may be used. In some embodiments, not all operations may be necessary.

Other embodiments, uses and advantages of the invention will be apparent to those skilled in the art from consideration of the specification and practice of the invention disclosed herein. The specification should be considered exemplary only, and the scope of the invention is accordingly intended to be limited only by the following claims.

What is claimed is:

1. An apparatus for utilizing an image of a lung of a patient and a target, the apparatus comprising:
   a tracking device for obtaining coordinates of a plurality of positions of each of a plurality of first and second elements, each element providing coordinates of its position;

a tracked navigation instrument having one or more of the plurality of first elements thereon for insertion into the lung of the patient to produce accuracy coordinates of the positions of the one or more first elements when the tracked navigation instrument touches one or more known locations or fiducials on the patient, the accuracy coordinates verify accuracy of the image;

a motion compensation device having one or more of the plurality of second elements thereon for insertion into the tracked navigation instrument;

a computing device for mitigating an effect of patient movement on the image by
producing an initial alignment of coordinates of the image with the accuracy coordinates,
maintaining the alignment of the coordinates of the image with the coordinates of the positions of the second elements, and
showing on the image the tracked navigation instrument as it is advanced to the target and the motion compensation device as it is advanced over the tracked navigation instrument to the target.

2. The apparatus of claim 1, the tracking device comprising an electromagnetic tracking device.

3. The apparatus of claim 1, wherein the motion compensation device is selected from a dynamic referencing device, a respiratory gating device, a spirometer, a breath temperature sensor, an oxygen sensor, a carbon dioxide sensor, a signal from a respirator, an extensometer, an electrocardiograph, and a cardiac gating device and wherein the motion compensation device is configured to provide the coordinates of the positions of the first and second elements to adjust registration of a patient's anatomy including the lung and improve accuracy of the displayed tracked navigation instrument.

4. The apparatus of claim 3, wherein the coordinates of the positions of the second elements are used to compensate for motion of the patient.

5. The apparatus of claim 1, wherein the tracked navigation instrument has a bent tip and is configured to be navigated to the target by manipulating the bent tip to point into a passageway of the lung leading to the target, while a position of the bent tip in the lung as indicated by the coordinates is displayed.

6. The apparatus of claim 1, wherein the tracked navigation instrument is selected from a guidewire, a catheter, a needle, a biopsy device, a brush, a laser device, a grasping device, an irrigation device, a radio frequency ablation device, and an ultrasound probe.

7. The apparatus of claim 1, further comprising a medical instrument selected from a catheter, a needle, a biopsy device, a brush, a laser device, a grasping device, an irrigation device, a radio frequency ablation device, and an ultrasound probe.

8. The apparatus of claim 7, wherein the medical instrument is configured to be inserted into the body of the patient.

9. The apparatus of claim 1, wherein the tracked navigation instrument is inserted through a lumen, the lumen is sized to slidably constrain the tracked navigation instrument to prevent the tracked navigation instrument from buckling while sliding within the lumen.

10. A method for utilizing an image of a lung of a patient and a target, the method comprising acts of:
registering anatomy of the patient by
inserting a tracked navigation instrument having one or more first elements thereon into the lung of the patient to produce accuracy coordinates of the positions of the one or more first elements when the tracked navigation instrument touches one or more known locations or fiducials on the patient, the accuracy coordinates verify accuracy of the image, each first element providing coordinates of its position, and
sampling by a tracking device the one or more first elements to obtain the coordinates of a plurality of positions of the one or more first elements;
maintaining registration of the anatomy of the patient by
inserting a motion compensation device having one or more second elements thereon into the tracked navigation instrument, and
sampling by the tracking device the one or more second elements to obtain the coordinates of a plurality of positions of the one or more second elements; and
a computing device mitigating an effect of patient movement on the image by
producing an initial alignment of coordinates of the image with the accuracy coordinates,
maintaining the alignment of the coordinates of the image with the coordinates of the positions of the second elements, and
displaying on the image the tracked navigation instrument and the motion compensation device advancing over the tracked navigation instrument to the target, after the tracked navigation instrument reaches the target.

11. The method of claim 10, wherein the tracking device comprises an electromagnetic tracking device.

12. The method of claim 10, wherein the tracked navigation instrument is inserted through a lumen comprising a bronchoscope.

13. The method of claim 10, wherein the motion compensation device is selected from one of: a dynamic referencing device, a respiratory gating device, a spirometer, a breath temperature sensor, an oxygen sensor, a carbon dioxide sensor, a signal from a respirator, an extensometer, an electrocardiograph, or a cardiac gating device and wherein the motion compensation device is configured to provide the coordinates of the positions of the elements to adjust registration of a patients anatomy including the lung and improve accuracy of the displayed position of the tracked navigation instrument.

14. The method of claim 10, further comprising an act of: displaying the position of the tracked navigation instrument in the lung on the display device,
wherein coordinates of the positions of the elements compensate for motion of the patient while displaying the position of the tracked navigation instrument in the lung.

15. The method of claim 10, wherein the tracked navigation instrument includes a bent tip.

16. The method of claim 15, comprising acts of:
manipulating the bent tip to point into a passageway of the lung leading to the target while viewing a position of the bent tip on the display of the tracked navigation instrument in the lung; and
advancing the tracked navigation instrument into the passageway towards the target.

17. The method of claim 10, wherein the target is selected from a lesion, a mass, and a tumor.

18. The method of claim 10, wherein the tracked navigation instrument is selected from a guidewire, a catheter, a needle, a biopsy device, a brush, a laser device, a grasping device, an irrigation device, a radio frequency ablation device, and an ultrasound probe.

19. The method of claim 10, further comprising an act of guiding a medical instrument to the target in the lung of the patient, the medical instrument is selected from a catheter, a needle, a biopsy device, a brush, a laser device, a grasping device, an irrigation device, a radio frequency ablation device, and an ultrasound probe.

20. The method of claim 19, wherein the medical instrument is inserted in to an interior of the patient.

21. A method for guiding a medical instrument to a target in a lung of a patient utilizing an image of the lung and the target, the method comprising acts of:
- generating a registration transformation of a first coordinate system of at least one image of the lung and a second coordinate system of position information regarding the lung by
  - inserting a tracked navigation instrument having one or more first elements thereon into the lung to produce accuracy coordinates of the positions of the one or more first elements when the tracked navigation instrument touches one or more known locations or fiducials on the patient, the accuracy coordinates verify accuracy of the image, and
  - sampling by a tracking device the one or more first elements to obtain the coordinates of a plurality of positions of the one or more first elements;
- generating by a computing device a display of the tracked navigation instrument in the lung using the at least one image of the lung and the registration transformation including the accuracy coordinates;
- navigating the tracked navigation instrument to the target using the display of the tracked navigation instrument in the lung;
- mitigating an effect of patient movement on the display by re-generating the registration transformation of the second coordinate system by inserting into the lung a motion compensation device having one or more second elements readable by the tracking device to obtain coordinates of a plurality of positions of the one or more second elements;
- re-generating, by the computing device, the display using the at least one image of the lung and the re-generated registration transformation;
- advancing a catheter over the tracked navigation instrument to the target after the tracked navigation instrument reaches the target; and
- navigating the medical instrument to the target through the catheter using the re-generated display.

* * * * *